(12) United States Patent
Scheib et al.

(10) Patent No.: US 11,166,722 B2
(45) Date of Patent: Nov. 9, 2021

(54) SURGICAL STAPLE CARTRIDGE WITH COMPRESSION FEATURE AT KNIFE SLOT

(71) Applicant: Ethicon LLC, Guaynabo, PR (US)

(72) Inventors: Charles J. Scheib, Loveland, OH (US); Jeffrey S. Swayze, West Chester, OH (US); Adam R. Dunki-Jacobs, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 296 days.

(21) Appl. No.: 16/417,832

(22) Filed: May 21, 2019

(65) Prior Publication Data

US 2019/0328388 A1 Oct. 31, 2019

Related U.S. Application Data

(62) Division of application No. 14/810,786, filed on Jul. 28, 2015, now Pat. No. 10,314,580.

(51) Int. Cl.
*A61B 17/072* (2006.01)
*A61B 17/00* (2006.01)
*A61B 17/29* (2006.01)

(52) U.S. Cl.
CPC .......... *A61B 17/07207* (2013.01); *A61B 2017/00398* (2013.01); *A61B 2017/00862* (2013.01); *A61B 2017/07257* (2013.01); *A61B 2017/07271* (2013.01); *A61B 2017/2927* (2013.01); *A61B 2017/2929* (2013.01)

(58) Field of Classification Search
CPC ............ A61B 17/07207; A61B 17/068; A61B 2017/07271

USPC ....................................................... 227/176.1
See application file for complete search history.

(56) References Cited

U.S. PATENT DOCUMENTS

| | | | |
|---|---|---|---|
| 4,805,823 | A | 2/1989 | Rothfuss |
| 5,014,899 | A | 5/1991 | Presty et al. |
| 5,415,334 | A | 5/1995 | Williamson et al. |
| 5,441,193 | A | 8/1995 | Gravener |
| 5,465,895 | A | 11/1995 | Knodel et al. |

(Continued)

FOREIGN PATENT DOCUMENTS

| | | |
|---|---|---|
| CN | 101507634 A | 8/2009 |
| CN | 101534725 A | 9/2009 |

(Continued)

OTHER PUBLICATIONS

European Search Report, Extended, and Written Opinion dated Nov. 11, 2016 for Application No. 16181400.9, 10 pages.

(Continued)

*Primary Examiner* — Michelle Lopez
(74) *Attorney, Agent, or Firm* — Frost Brown Todd LLC

(57) ABSTRACT

An apparatus includes a body, a shaft assembly, an end effector, and a staple cartridge. The end effector includes an anvil and a lower jaw. The anvil is pivotable toward the lower jaw to capture tissue between the anvil and the lower jaw. The staple cartridge is coupled with the lower jaw. The staple cartridge includes a deck and a plurality of staples. The deck faces the anvil. The anvil or the deck (or both) includes a compressible that extends toward the other of the anvil or the deck. The compressible feature of the anvil of the deck is configured to compress tissue against the other of the anvil or the deck.

20 Claims, 26 Drawing Sheets

(56) References Cited

U.S. PATENT DOCUMENTS

| | | | |
|---|---|---|---|
| 5,551,622 A * | 9/1996 | Yoon | A61B 17/072 227/176.1 |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney | |
| 7,691,098 B2 | 4/2010 | Wallace | |
| 7,721,930 B2 | 5/2010 | McKenna et al. | |
| 7,806,891 B2 | 10/2010 | Nowlin et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,579,178 B2 | 11/2013 | Holsten et al. | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,186,142 B2 | 11/2015 | Fanelli et al. | |
| 9,301,755 B2 | 4/2016 | Shelton, III et al. | |
| 9,301,759 B2 | 4/2016 | Spivey et al. | |
| 9,517,065 B2 | 12/2016 | Simms et al. | |
| 10,130,359 B2 | 11/2018 | Hess et al. | |
| 10,314,580 B2 | 6/2019 | Scheib et al. | |
| 2009/0120994 A1* | 5/2009 | Murray | A61B 17/115 227/180.1 |
| 2012/0168487 A1 | 7/2012 | Holsten et al. | |
| 2013/0062391 A1 | 3/2013 | Boudreaux et al. | |
| 2013/0172929 A1 | 7/2013 | Hess et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2015/0272575 A1 | 10/2015 | Leimbach et al. | |
| 2015/0374360 A1 | 12/2015 | Scheib et al. | |
| 2015/0374373 A1 | 12/2015 | Rector et al. | |

FOREIGN PATENT DOCUMENTS

| | | |
|---|---|---|
| CN | 103717151 A | 4/2014 |
| EP | 2764 833 A2 | 8/2014 |
| JP | 2013-223765 A | 10/2013 |
| JP | 2015-512720 A | 4/2015 |

OTHER PUBLICATIONS

European Examination Report dated Jan. 4, 2018 for Application No. 16181400.9, 5 pages.
Extended European Search Report dated Aug. 27, 2019 for Application No. 19173116.5, 7 pages.
International Search Report and Written Opinion dated Nov. 9, 2016 for International Application No. PCT/US2016/042731, 16 pages.
Chinese Office Action and Search Report dated Mar. 27, 2020 for Application No. 201680043714.8, 5 pages.
Japanese Notification of Reasons for Refusal dated May 22, 2020, and Search Report by Registered Search Organization completed Apr. 20, 2020 for Application No. 2018-504168, 19 pages.

* cited by examiner

SURGICAL STAPLE CARTRIDGE WITH COMPRESSION FEATURE AT KNIFE SLOT

This application is a divisional of U.S. patent application Ser. No. 14/810,786, filed Jul. 28, 2915 and issued as U.S. Pat. No. 10,314,580 on Jun. 11, 2019.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,479 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
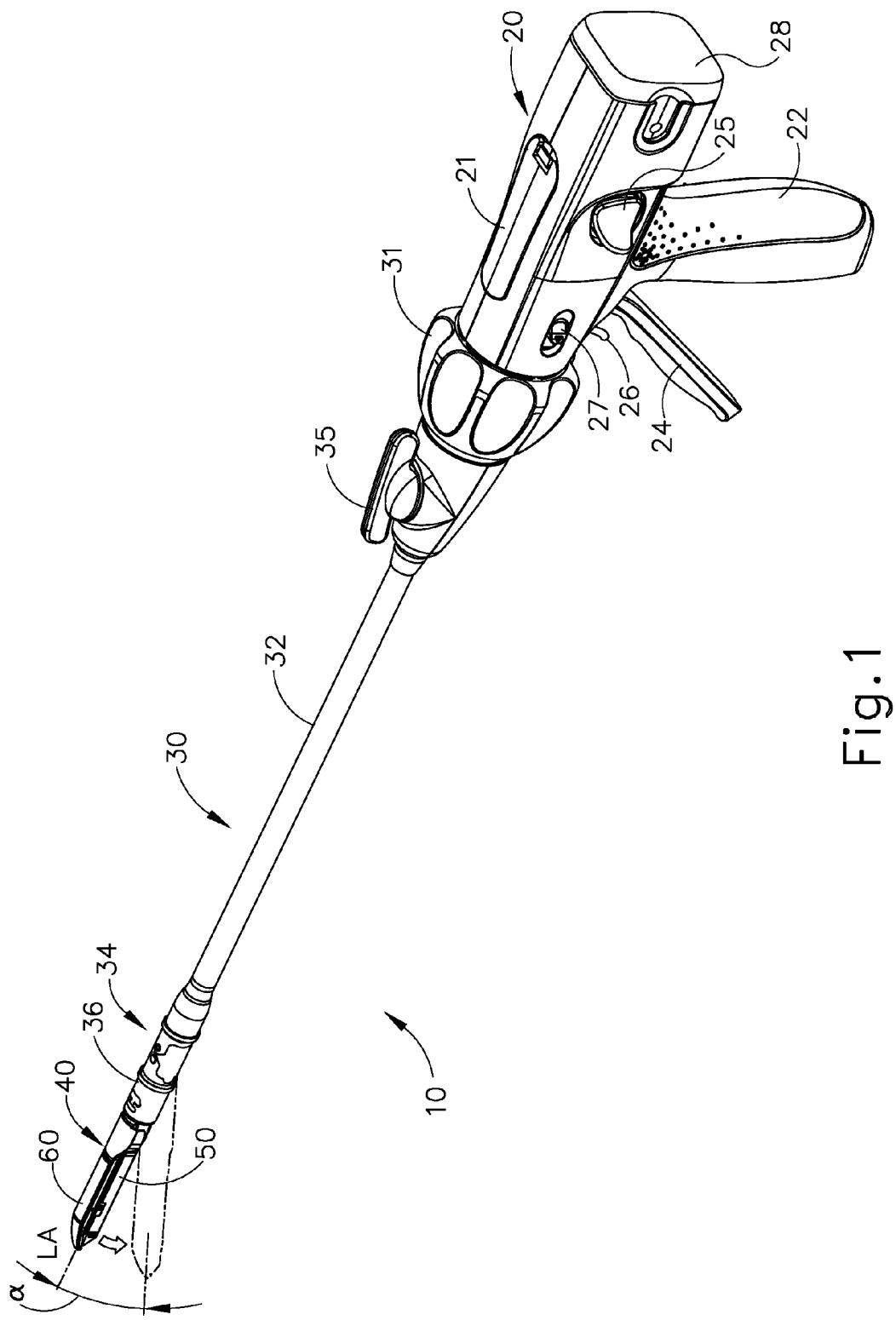
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
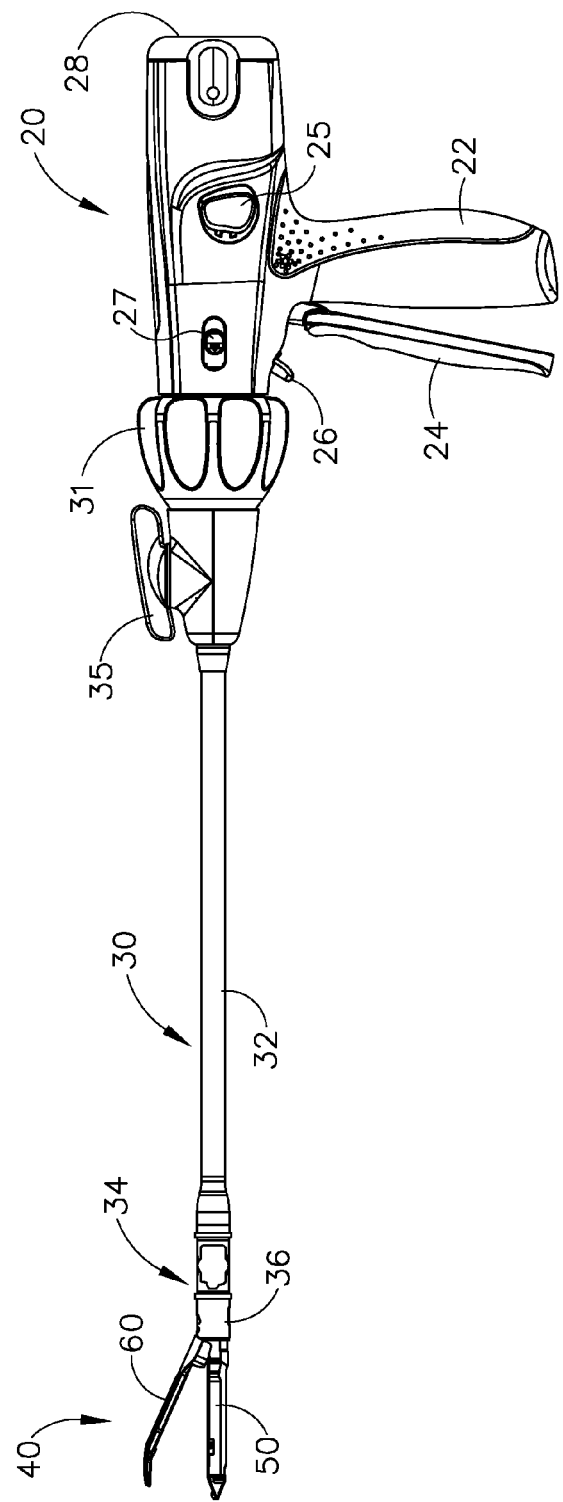
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
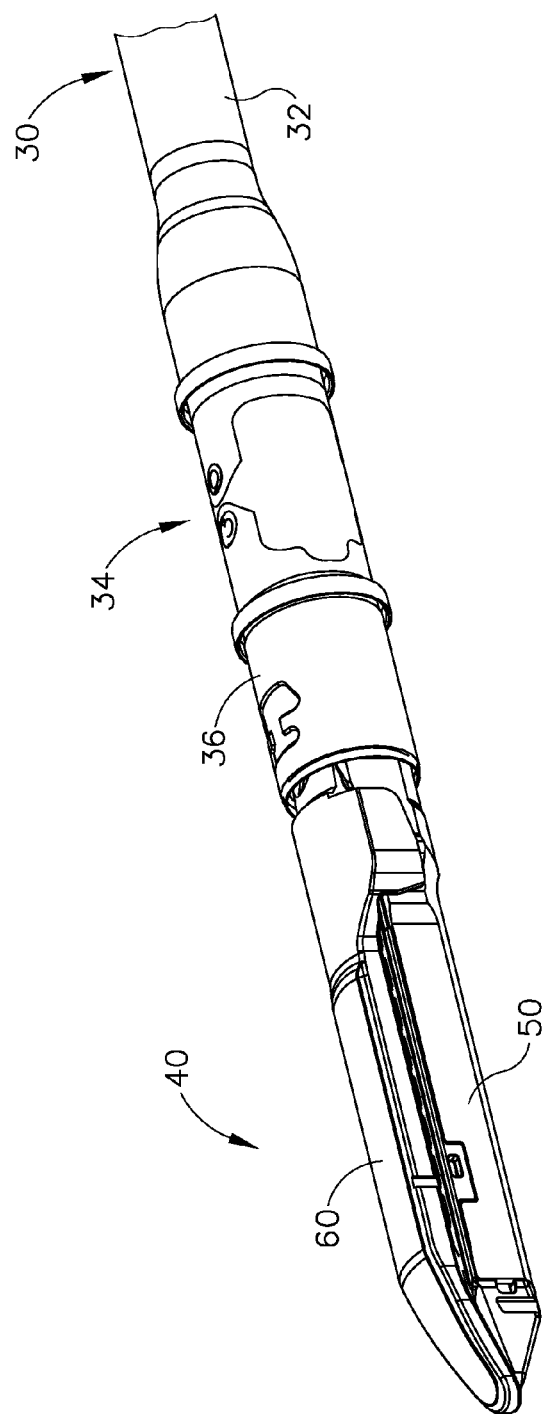
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, published as U.S. Pub. No. 2015/0374360 on Dec. 31, 2015, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw

(50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 4:
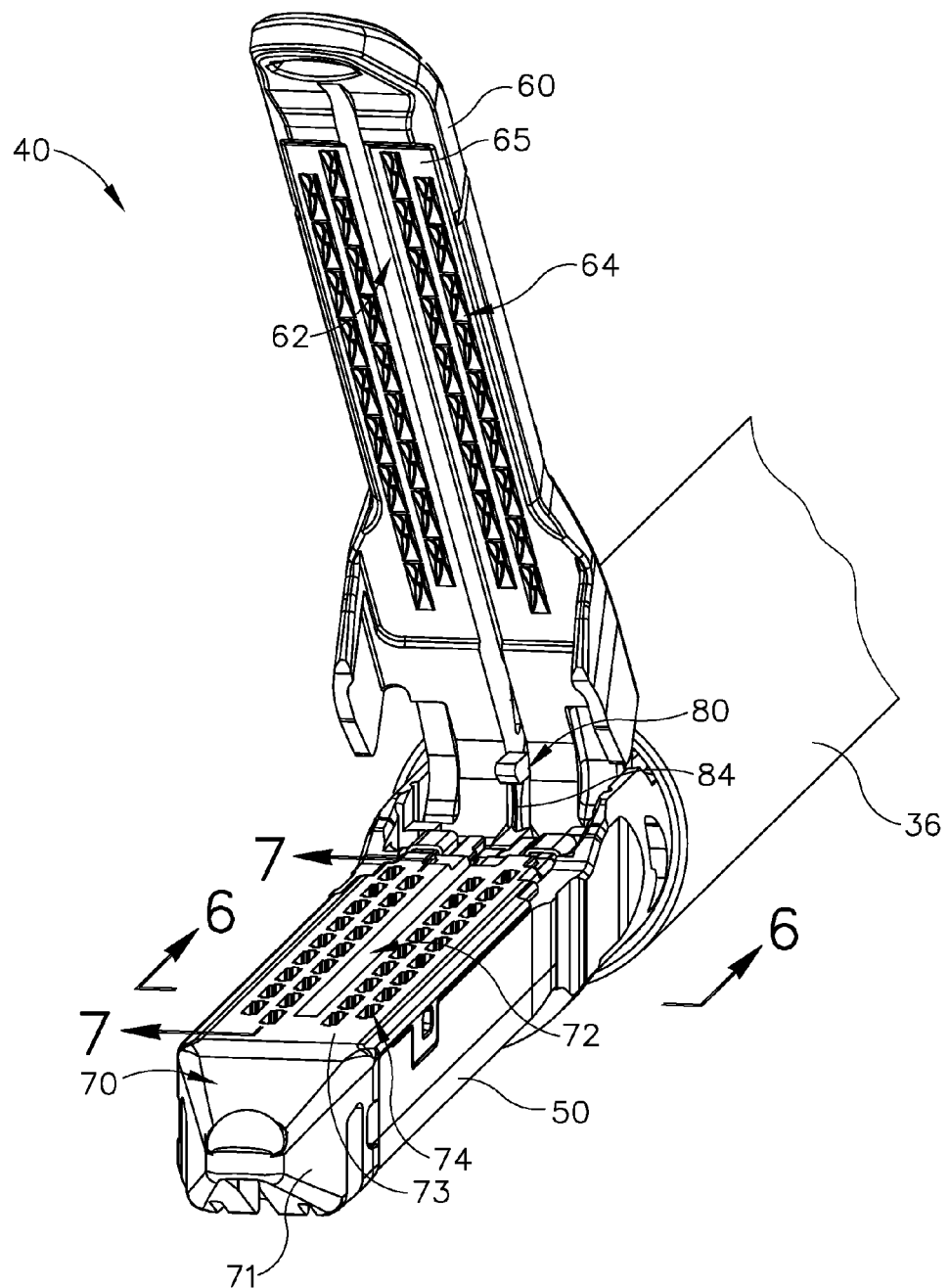
FIG. 4 depicts a perspective view of the end effector of FIG. 3, with the end effector in an open configuration.
Figure 5:
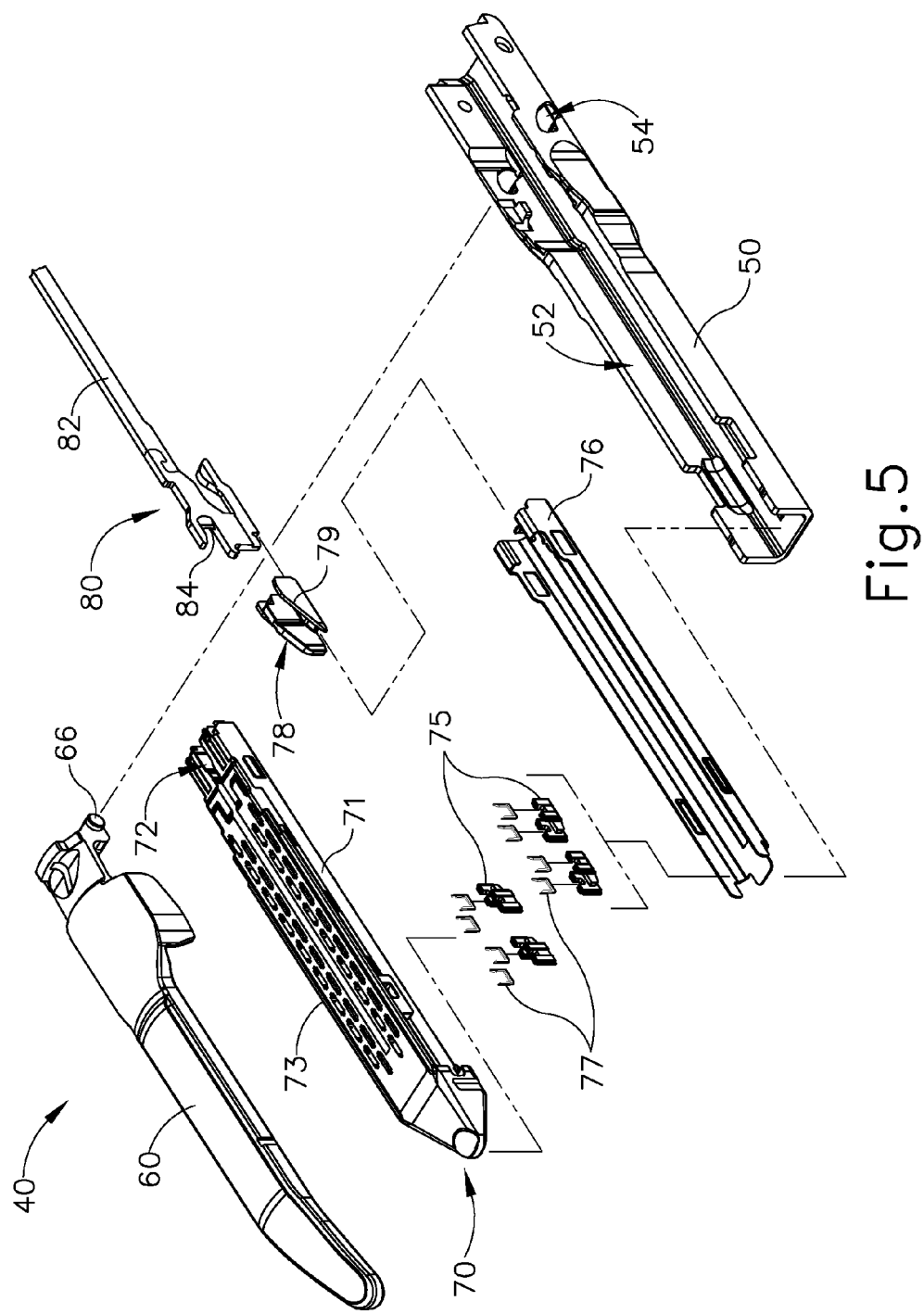
FIG. 5 depicts an exploded perspective view of the end effector of FIG. 3.
Figure 6:
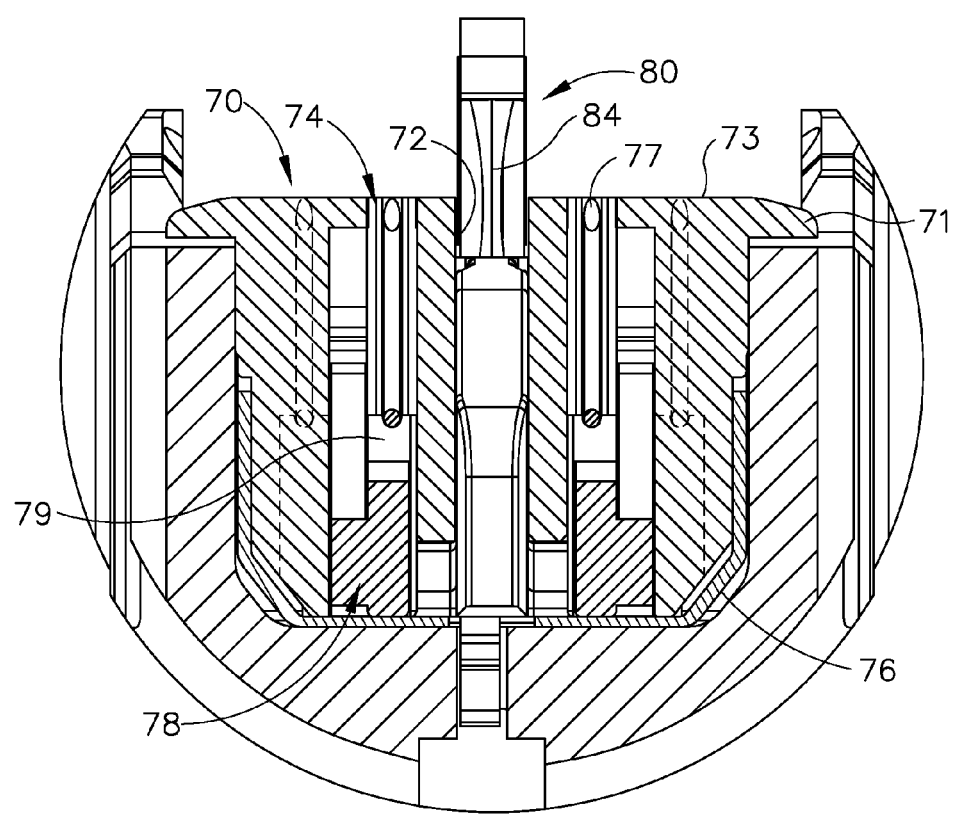
FIG. 6 depicts a cross-sectional end view of the end effector of FIG. 3, taken along line 6-6 of FIG. 4.
Figure 7A:
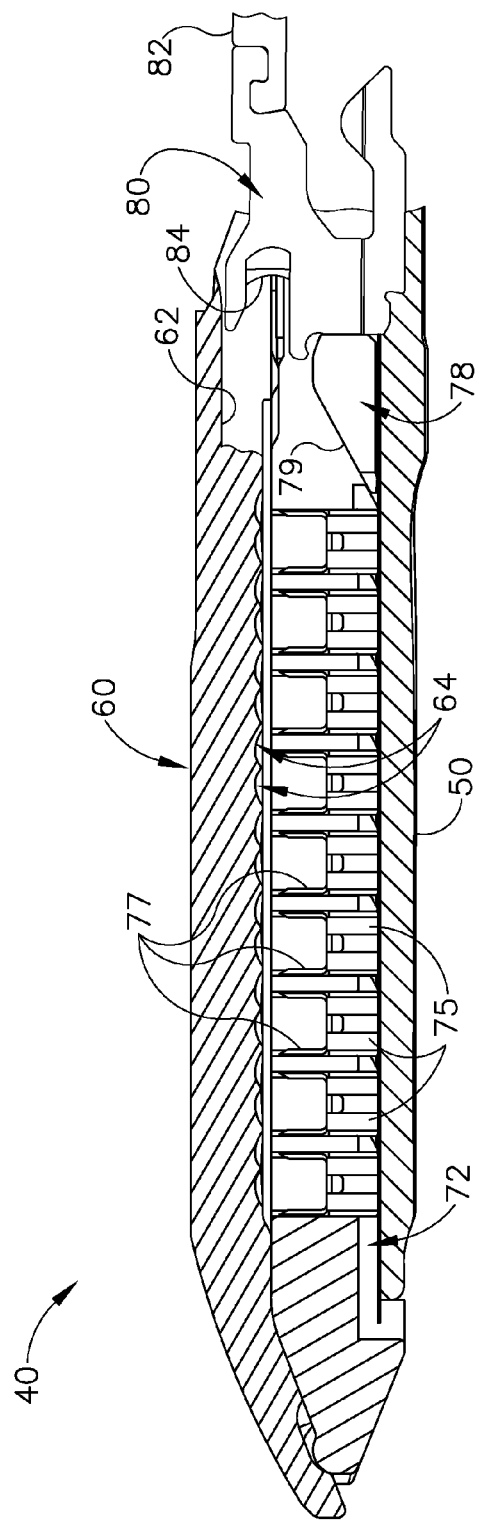
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
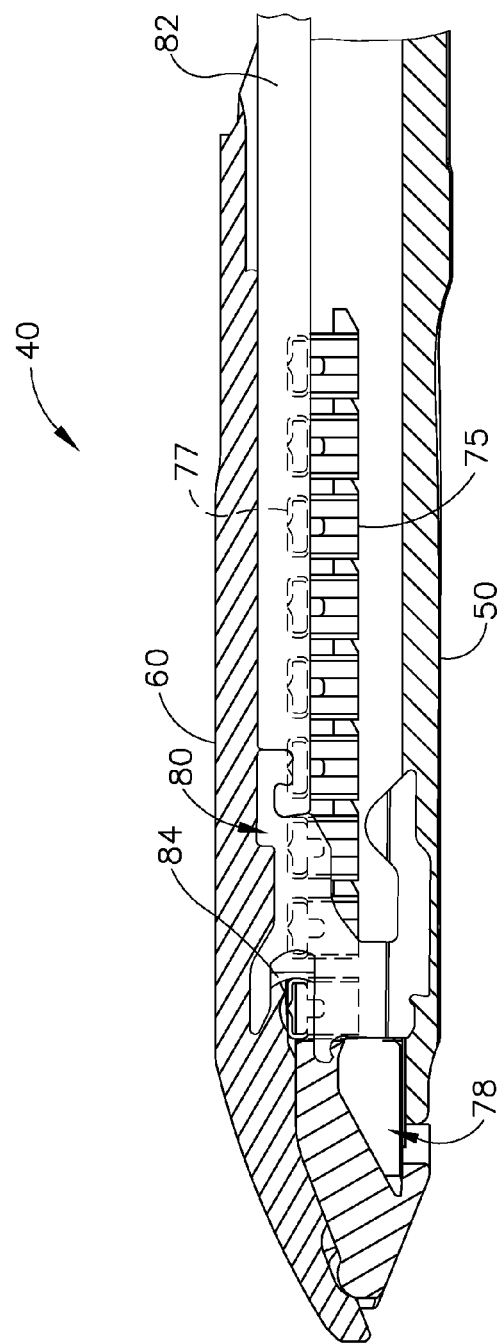
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, issued as U.S. Pat. No. 9,717,479 on Aug. 1, 2017 the disclosure of which is incorporated by reference herein; and/or at least some of the teachings of U.S. patent application Ser. No. 14/314,108, entitled "Method of Using Lockout Features for Surgical Staple cartridge," filed on Jun. 25, 2014, published as U.S. Pub. No. 2015/0374373 on Dec. 31, 2015, issued as U.S. Pat. No. 10,335,147 on Jul. 2, 2019, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373 on Dec. 31, 2015, issued as U.S. Pat. No. 10,335,147 on Jul. 2, 2019, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

Figure 8:
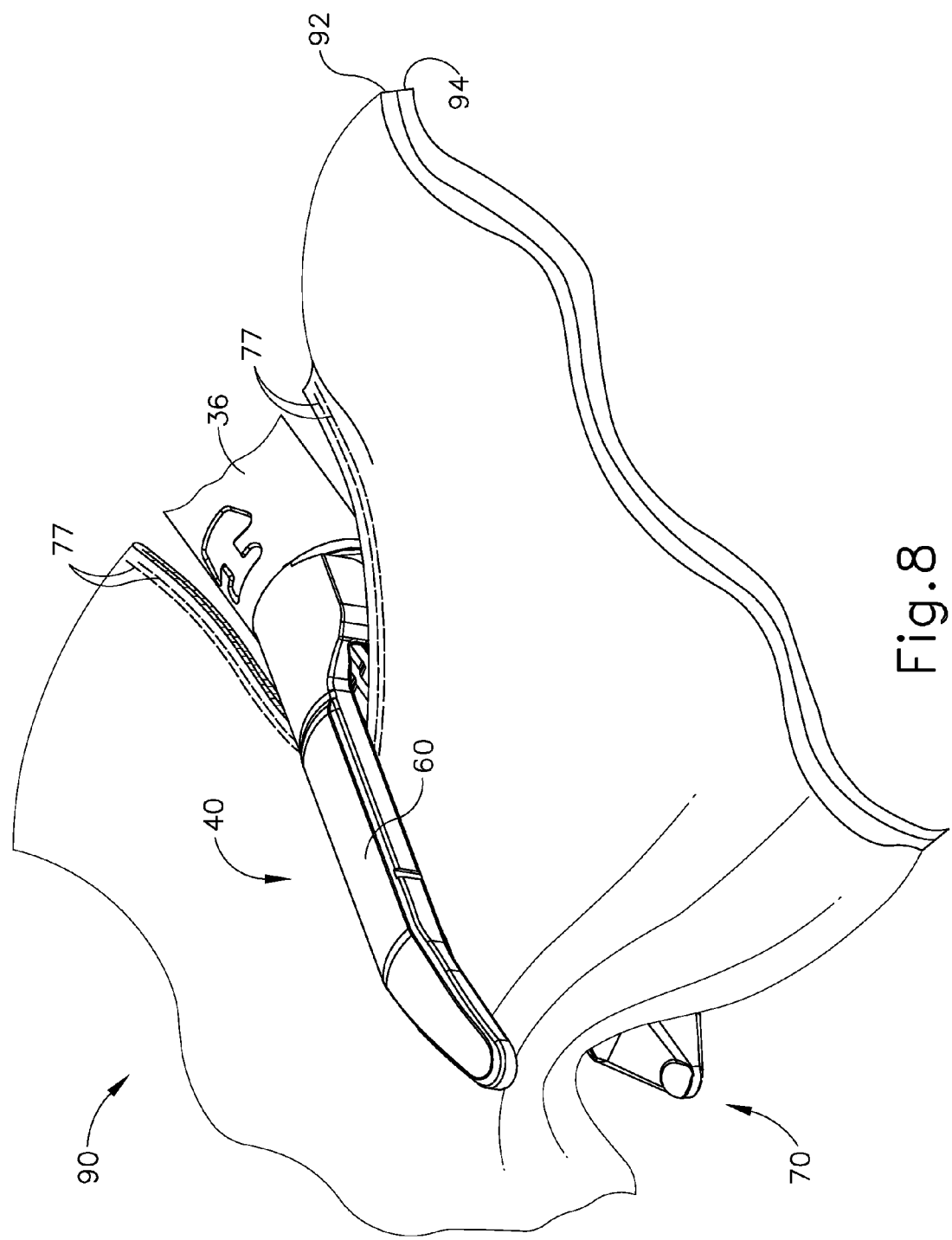
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative End Effectors with Compressible Features on Jaws

End effector (40) may be structured to provide a predefined gap separating the surface of cartridge deck (73) and the corresponding surface of anvil (60) when anvil (60) is in a closed position. In some instances, cutting and stapling tissue may be challenging if the thickness of the target tissue differs from this predefined gap distance. For example, if the target tissue is significantly thicker than the gap, an operator may have trouble firing the instrument to effectively cut and staple the tissue. On the other hand, if the target tissue is thinner than the gap between the cartridge deck and the anvil, it may be difficult to maintain the position of the target tissue between anvil (60) and deck (73). Particularly, during firing, as knife member (80) advances against the tissue, the tissue may shift position within the jaws of the instrument, thereby making it challenging to effectively cut the target tissue. In some instances, staples (77) are driven through regions of tissue before knife member (80) reaches the same regions of tissue, such that the legs of staples (77) are disposed in the tissue before that region of tissue is severed. In such instances where the tissue is so thin that the tissue is not being held in place due to compression between anvil (60) and deck (73), knife member (80) may plow the tissue rather than cutting it cleanly, which may result in staples (77) tearing through the tissue through a cheese wire effect.

In view of the foregoing, it may be desirable to provide one or more features in end effector (40) that compress relatively thin tissue to thereby secure the tissue as knife member (80) is actuated. Such compression of tissue may prevent undesirable movement of tissue that might otherwise occur when the tissue is positioned between a closed anvil (60) and deck (73). In some versions, the compression features are present on staple cartridge (70), anvil (60), or both, as discussed in further detail below. By holding target tissue in place during firing of knife member (80), such compression features will aid in an effective cutting and stapling of tissue, even where the target tissue is thinner than the predefined gap distance between anvil (60) and deck (73) when anvil (60) is in a closed position. Several examples of tissue compression features are described in greater detail below, while other examples will be apparent to those of ordinary skill in the art in view of the teachings herein.

FIGS. 9A-16C show different examples of end effectors (140, 240, 340, 440) that include an anvil (60, 460) and a lower jaw (50, 150, 250, 350). Anvil (60) is omitted from FIGS. 9A-9B, 11, and 13 for clarity. Lower jaw (50, 150, 250, 350) includes an exemplary alternative staple cartridge (70, 170, 270, 370). End effector (140, 240, 340, 440) may be readily incorporated into instrument (10) in place of end effector (40). Except as otherwise described below, end effector (140, 240, 340, 440) is configured and operable just like end effector (40) described above. For instance, knife member (80) may be driven through end effector (140, 240, 340, 440) just like knife member (80) being driven through end effector (40) as described above.

Staple cartridges (170, 270, 370) and anvil (460) of the present example include at least one compressible feature that aids in applying compressive force to the target tissue clamped between anvil (60, 460) and lower jaw (50, 150, 250, 350), to thereby hold the target tissue in place. In the examples shown, at least a portion of the target tissue is thinner than the predefined gap distance defined between anvil (60, 460) and lower jaw (50, 150, 250, 350) when anvil (60, 460) is in the closed position. However, it will be understood that the end effectors (140, 240, 340, 440) are suitable for use with a variety of tissue thicknesses, including tissue that is thicker than the predefined gap distance between anvil (60, 460) and deck (73) when anvil (60, 460) is in a closed position.

A. Exemplary Staple cartridge with Severable Compressible Feature Along Knife Slot FIGS. 9A-10C show an exemplary alternative end effector (140). As discussed above, end effector (140) is configured to operate substantially similarly to end effector (40), except for the differences described below. End effector (140) comprises anvil (60) and lower jaw (50). Anvil (60) is omitted from FIGS. 9A-9B for clarity. An exemplary alternative staple cartridge (170) is disposed in lower jaw (50). Staple cartridge (170) is configured to operate in a substantially similar manner as discussed with respect to staple cartridge (70). However, staple cartridge (170) of this example includes a compressible feature (196) disposed along longitudinal channel (72) of cartridge (170).

Figure 10A:
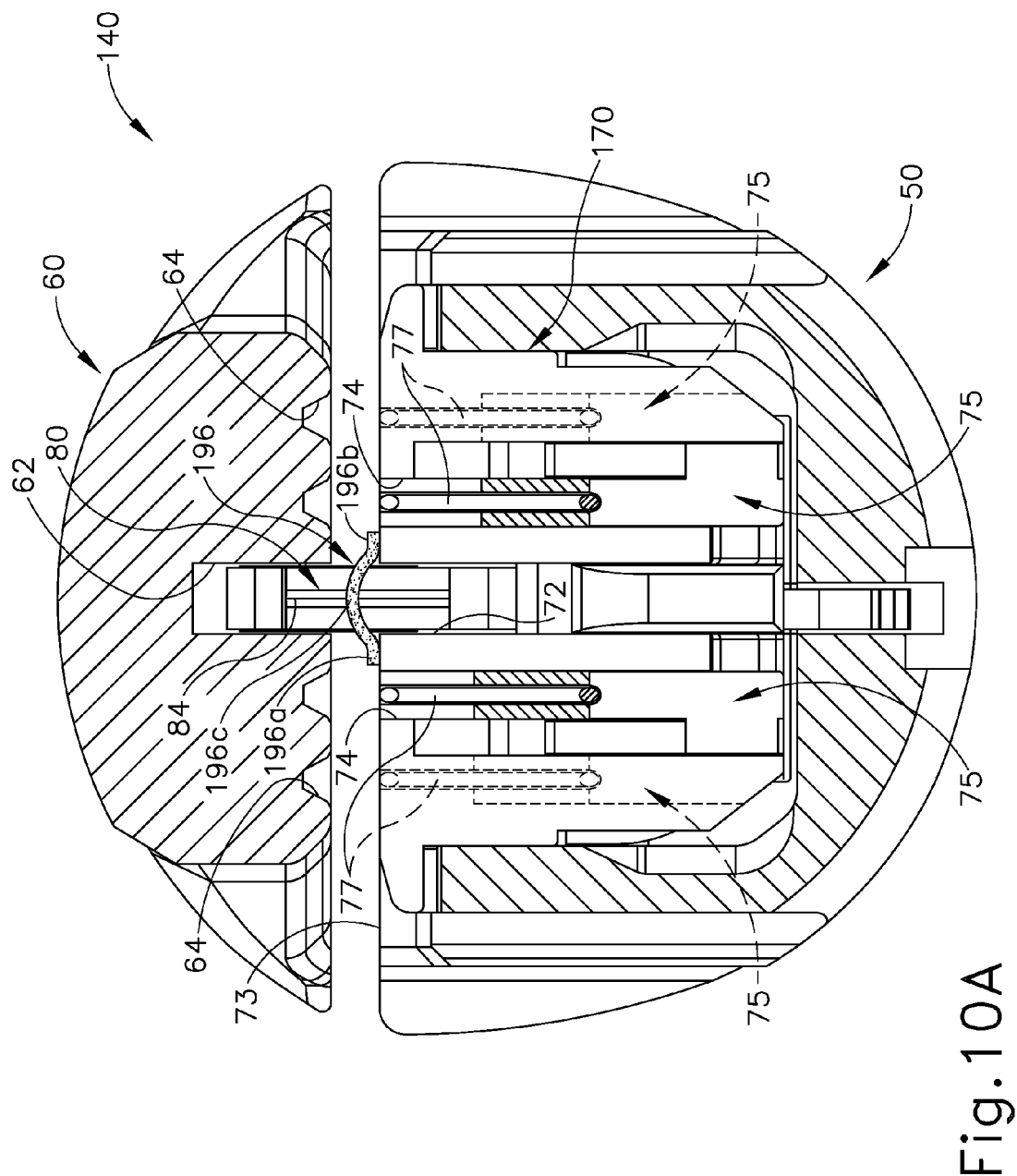
FIG. 10A depicts a cross-sectional view of the end effector of FIG. 9A, taken along line 10-10 of FIG. 9A, with the firing beam in the proximal position.

Compressible feature (196) is configured to urge tissue that is captured between the anvil (60) and lower jaw (50) toward anvil (60). Particularly, compressible feature (196)

includes a first side (196a) that is fixed to cartridge deck (73) on one side of channel (72), a second side (196b) that is fixed to cartridge deck (73) on another side of channel (72), and a middle portion (196c) extending between the first and second sides (196a, 196b). Therefore, in the present example, compressible feature (196) bridges channel (72). As shown, compressible feature (196) has a cross-sectional profile in the form of a curved C-shape (along a plane that is perpendicular to the longitudinal axis of instrument (10)), such that middle portion (196c) is spaced from cartridge deck (73). Particularly, as best seen in FIG. 10A, the distance between middle portion (196c) and cartridge deck (73) is less than the gap distance between cartridge deck (73) and anvil (60) when anvil (60) is in the closed position.

As shown in the present example, compressible feature (196) is formed as a single, elongate feature disposed substantially along the entire length and width of channel (72). However, in alternative examples, compressible feature (196) may be a formed as a plurality of discrete elements that are spaced apart from each other along the length of channel (72). Furthermore, in some examples, compressible feature (196) extends only along a portion or certain portions of channel (72). Other suitable configurations and positions for compressible feature (196) will be apparent to persons skilled in the art in view of the teachings herein.

In the example shown, compressible feature (196) is formed as a separate element from cartridge deck (73) and is fixed to cartridge deck (73) at the first and second sides (196a, 196b) by various suitable methods as will be apparent to persons skilled in the art in view of the teachings herein. In some versions, compressible feature (196) may be overmolded onto the cartridge deck (73) or other parts of cartridge (170). In some versions, compressible feature (196) is integral with cartridge (170). In some such versions, compressible feature (196) may be co-molded with cartridge deck (73) or other parts of cartridge (170). In the example shown, compressible feature (196) is configured to be rigid enough to maintain its position and urge tissue toward anvil (60) when an operator grasps tissue between anvil (60) and lower jaw (50). However, compressible feature (196) is also configured to be compressible a sufficient amount such that when an operator grasps tissue (90) between lower jaw (50) and anvil (60), compressible feature (196) does not prevent anvil (60) from moving to the fully closed position relative to the lower jaw (50) (as, for example, shown in FIGS. 10B-10C). Other suitable configurations of compressive feature (196) will be apparent to persons skilled in the art in view of the teachings herein.

In some examples, compressible feature (196) may comprise a polymer and/or an elastomer. In addition or in the alternative, compressible feature (196) may be formed of a resilient material, such that compressible feature (196) resiliently biases tissue (90) against anvil (60) when tissue (90) is captured between anvil (60) and deck (73). Other suitable materials that may be used to form compressible feature (196) will be apparent to persons skilled in the art in view of the teachings herein. It should be understood that, due to the compressibility and/or other properties of compressible feature (196), compressible feature (196) will not cause any trauma to tissue (90) even when compressible feature (196) compresses the tissue (90) against anvil (60).

Figure 10B:
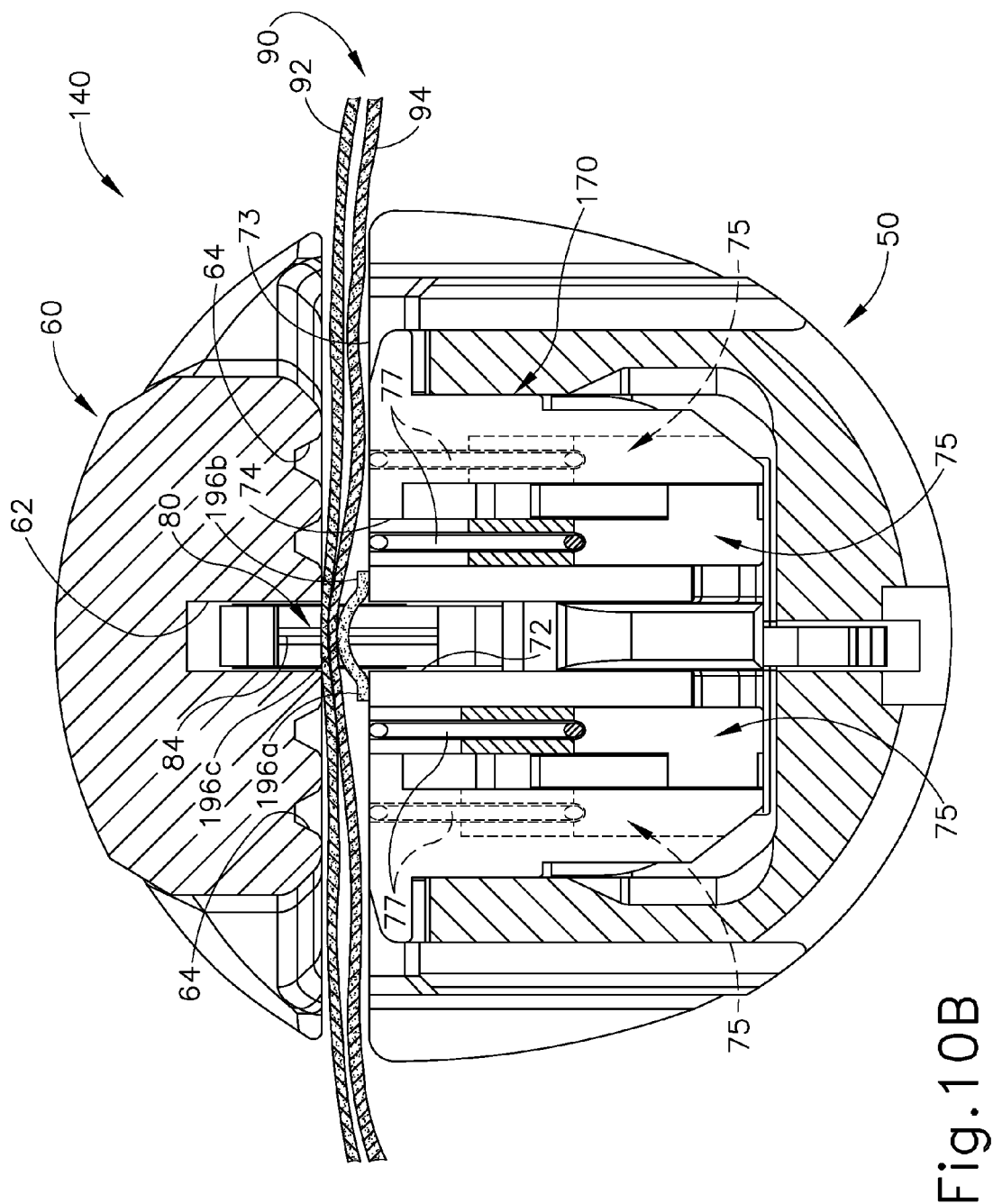
FIG. 10B depicts a cross-sectional view of the end effector of FIG. 9A, taken along line 10-10 of FIG. 9A, with the firing beam in a proximal position and tissue positioned between an anvil and a staple cartridge deck of the end effector.
Figure 10C:
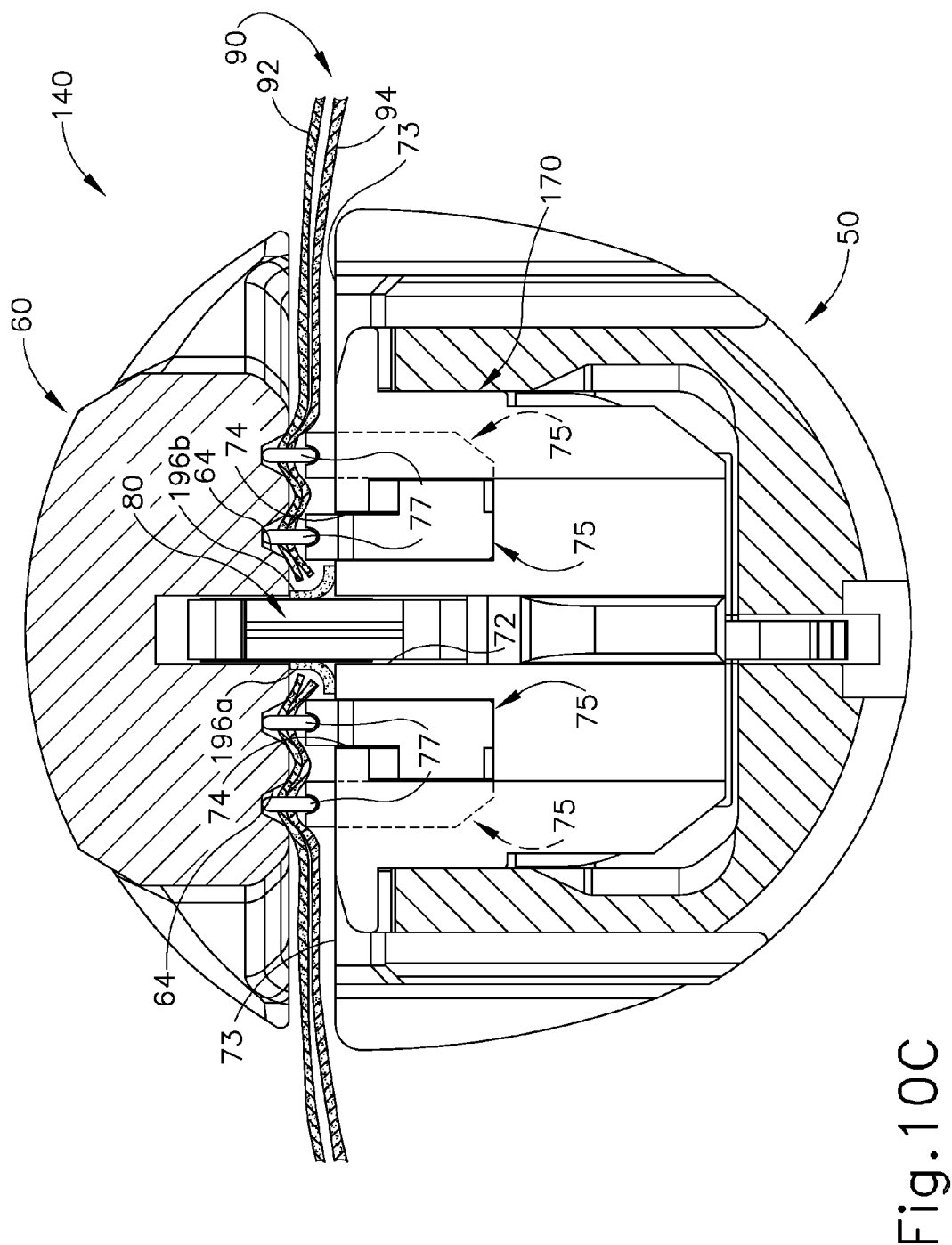
FIG. 10C depicts a cross-sectional view of the end effector of FIG. 9A, taken along line 10-10 of FIG. 9A, with the firing beam in a distal position and tissue positioned between the anvil and staple cartridge deck of the end effector.

Referring to FIGS. 10B-10C, in use, end effector (140) may clamp tissue in the same manner as described above with respect to end effector (40). As shown, the layers (92, 94) of tissue (90) are positioned between anvil (60) and lower jaw (50). In the example shown, the combined thickness of the layers (92, 94) of tissue (90) along at least a portion of the tissue (90) is less than the predefined gap distance between the anvil (60) and cartridge deck (73) when anvil (60) is in the closed position. However, compressible feature (196) applies a substantially vertical load to the tissue (90) that is coincident with the compressible feature (196), compressing the corresponding region of tissue (90) up against anvil (60).

Figure 9A:
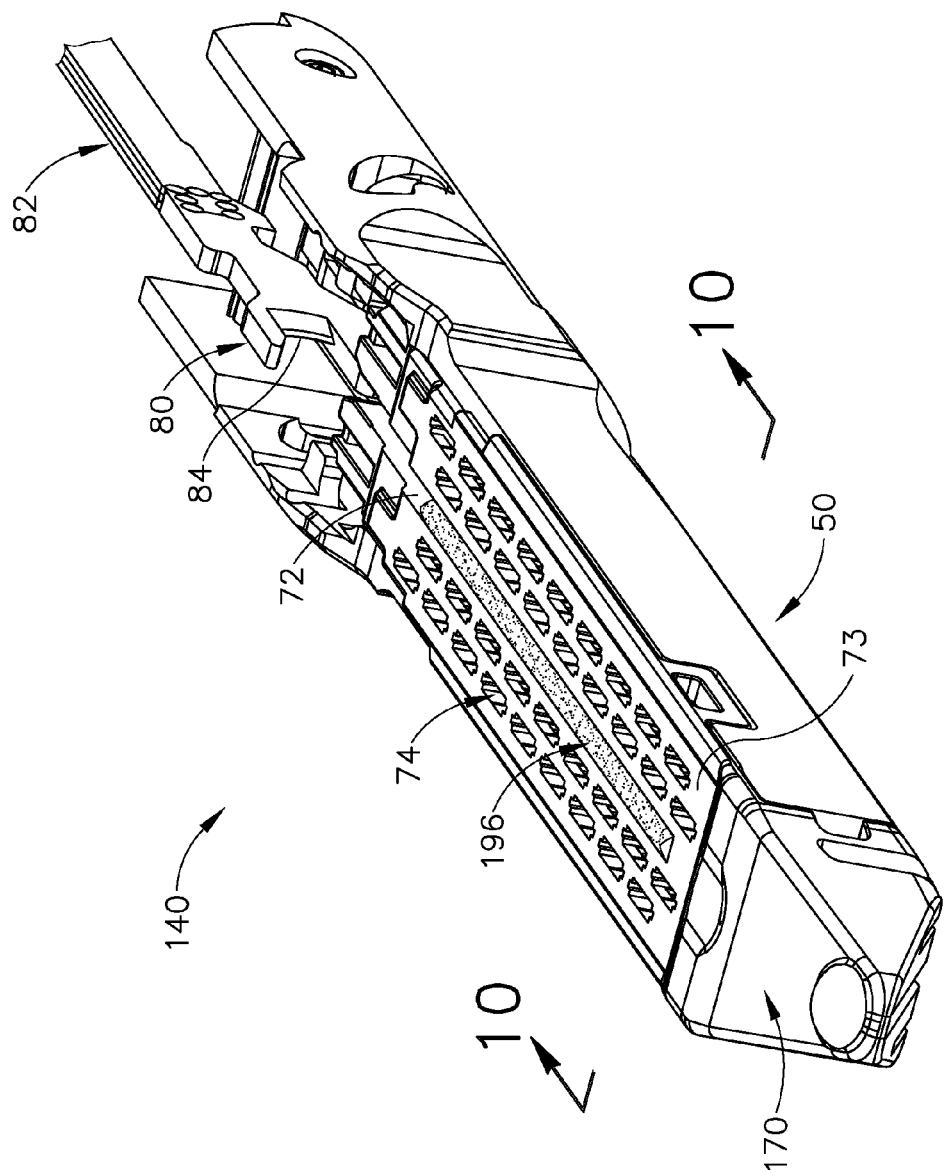
FIG. 9A depicts a perspective view of an exemplary alternative end effector that may be incorporated into the instrument of FIG. 1, with a firing beam in a proximal position.
Figure 9B:
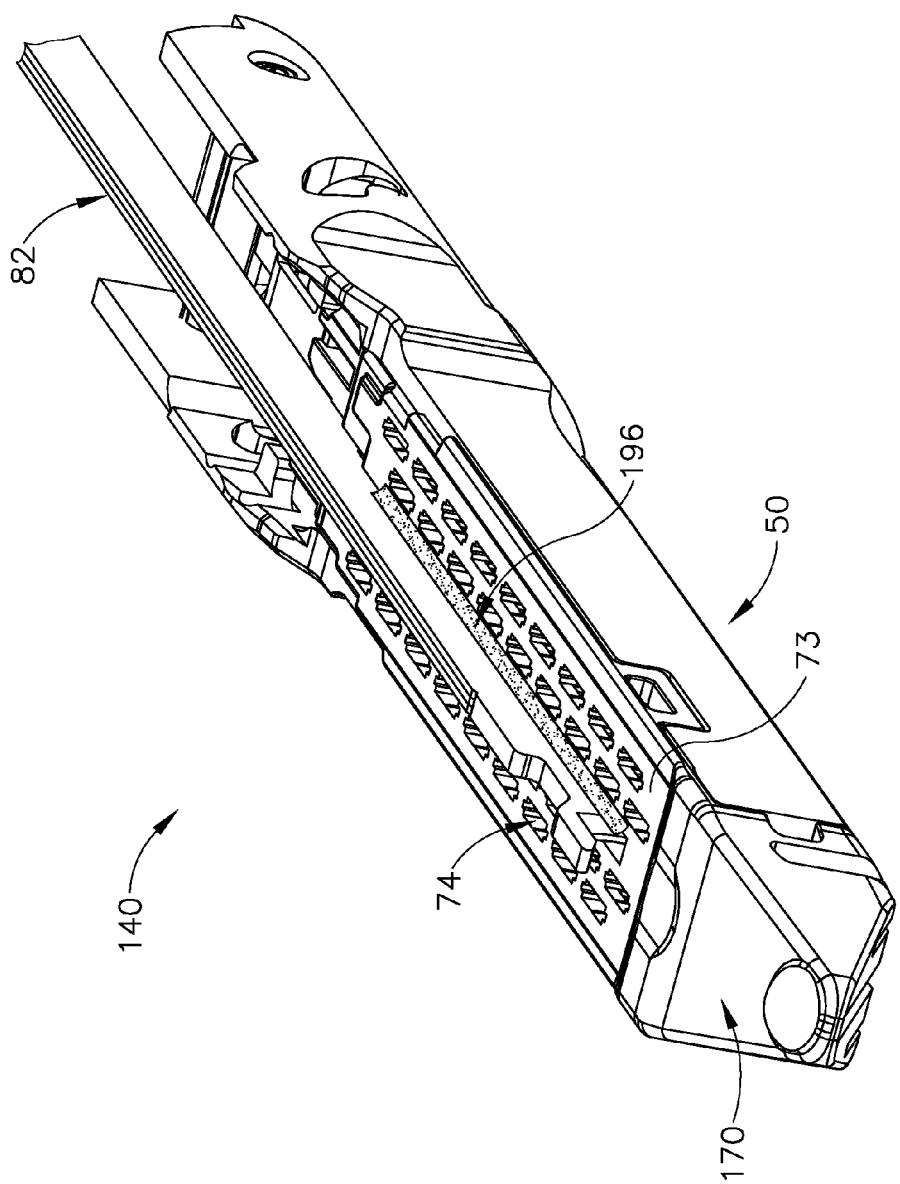
FIG. 9B depicts a perspective view of the end effector of FIG. 9A, with the firing beam in a distal position.

In the example shown, compressible feature (196) contacts a region of tissue (90) that is substantially aligned with channels (62, 72). As shown in FIGS. 9B and 10C, as knife member (80) advances along channels (62, 72), knife member (80) simultaneously severs tissue (90) and compressible feature (196), such that severed portions (196a, 196b) of compressible feature (196) are urged away from channel (72) and are positioned against respective lateral sides of knife member (80). Moreover, knife member (80) drives wedge sled (78) distally as knife member (80) translates distally through end effector (140), thereby driving staples (77) through tissue (90) and against anvil (60) into formation, in the same manner described above with respect to end effector (40).

As shown, compressible feature (196) prevents tissue (90) from substantially moving during the severing and stapling of tissue (90). In particular, by compressing tissue (90) against anvil (60), compressible feature (196) keeps the tissue (90) substantially stationary across the width of deck (73) and anvil (60), thereby preventing movement of tissue (90) along lateral paths that are transverse to the longitudinal axis of end effector (140). Moreover, compressible feature (196) prevents movement of tissue (90) along paths that are parallel to the longitudinal axis of end effector (140). By firmly holding the position of tissue (90) between anvil (60) and cartridge deck (73), compressible feature (196) may reduce stress that might otherwise be imposed on tissue (90), at the regions where legs of staples (77) are driven through tissue (90), as knife member (80) as driven through tissue. In other words, compressible feature (196), rather than staples (77), may serve the role of holding tissue (90) in place as knife member (80) cuts through the tissue (90). In the absence of compressible feature (196), when tissue (90) is thinner than the predefined gap separating the surface of cartridge deck (73) and the corresponding surface of anvil (60) when anvil (60) is in a closed position, staples (77) may need to serve the role of holding tissue (90) in place as knife member (80) cuts through the tissue (90), which may cause the tissue (90) to tear at staples (77) through a cheese wire effect. Such tearing may compromise the fixation of staples (77) in the tissue (90), which may ultimately result in full or partial failure of a deployed line of staples (77). Compressible feature (196) may thus maintain greater structural integrity of tissue (90) after end effector (140) has been actuated on the tissue (90); and may thus provide a more reliable line of staples (77) in the tissue.

In some versions, knife member (80) may include at least one feature that directs the severed portions of compressible feature (196) away from tissue (90) to prevent compressible feature (196) from substantially interfering with further advancement of knife member (80). Moreover, in some examples, knife member (80) and/or compressible feature (196) may include a lubricious coating to prevent compressible feature (196) from substantially interfering with further advancement of the knife member (80). Other suitable configurations of compressible feature (196) will be apparent to persons skilled in the art in view of the teachings herein.

While compressible feature (196) is shown as being part of cartridge (170) in the present example, it should be understood that one or more similar compressible features may be readily incorporated into anvil (60). In versions where anvil (60) includes an integral compressible feature like compressible feature (196), cartridge (170) may still include compressible feature (196). In some such versions, the compressible feature(s) of anvil (60) may be laterally offset from compressible feature (196) of cartridge (170). In some other versions where anvil (60) includes one or more integral compressible features like compressible feature (196), cartridge (170) may simply lack compressible feature (196). Cartridge (170) may also include more than one compressible feature (196) at any suitable positions along the width of deck (73). It should also be understood that, regardless of whether the compressible feature(s) is/are on anvil (60) and/or on cartridge (170), end effector (140) may be used as a tissue grasper by selectively opening and closing anvil (60), even with thin tissue structures, without necessarily firing knife member (80). Other suitable ways in which compressible feature (196) may be varied and used will be apparent to those of ordinary skill in the art in view of the teachings herein.

Figure 11:
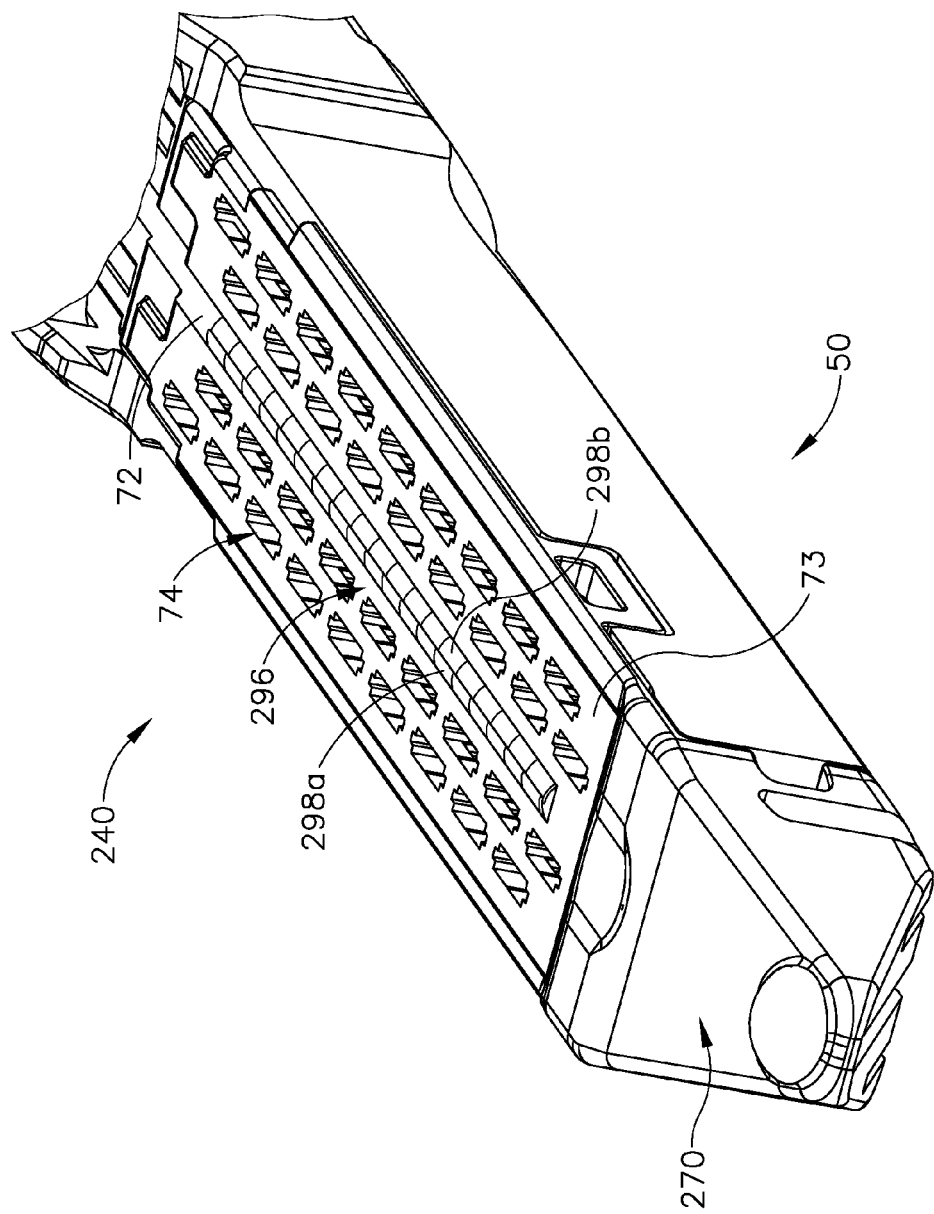
FIG. 11 depicts perspective view of another exemplary alternative end effector that may be incorporated into the instrument of FIG. 1, with an anvil of the end effector omitted for clarity.

B. Exemplary Staple Cartridge with Displaceable, Compressible Fins Along Knife Slot FIGS. 11-12C show another exemplary alternative end effector (240). As discussed above, end effector (240) is configured to operate substantially similarly to end effector (40), except for the differences described below. End effector (240) comprises anvil (60) and lower jaw (50). Anvil (60) is omitted from FIG. 11 for clarity. An exemplary alternative staple cartridge (270) is disposed in lower jaw (50). Staple cartridge (270) is configured to operate in a substantially similar manner as discussed with respect to staple cartridge (70). However, staple cartridge (170) of this example includes a compressible feature (296) disposed along longitudinal channel (72) of cartridge (270).

Compressible feature (296) is configured to urge tissue that is captured between anvil (60) and lower jaw (50) toward anvil (60). Compressible feature (296) of the present example comprises a pair of opposing fins (298a, 298b). Fin (298a) is fixed to cartridge deck (73) on one side of channel (72) and fin (298b) is fixed to cartridge deck (73) on another side of channel (72). As shown, each of the fins (298a, 298b) extends inwardly toward a central, longitudinally extending vertical plane of end effector (240). Fins (298a, 298b) thus together bridge channel (72). In addition, fins (298a, 298b) extend upwardly toward anvil (60), such that compressible feature (296) is configured to urge tissue captured between the anvil (60) and lower jaw (50) toward anvil (60).

In the present example, fins (298a, 298b) are in contact with one another. Prior to knife member (80) advancing along channel (72), fin (298a) lies atop fin (298b) in a partially overlapping fashion. However, in other examples, fin (298b) may lie atop fin (298a). In other examples, one of fins (298a, 298b) may not lie atop the other. For example, fins (298a, 298b) may extend at least partially over channel (72) such that they are in contact but not overlapping one another, or such that they do not contact one another, for example.

Each fin (298a, 298b) is formed as a single, elongate feature disposed substantially along the entire length of channel (72). However, in alternative examples, one or both of fins (298a, 298b) may be formed as a plurality of discrete elements that are spaced apart from each other along the length of channel (72). Furthermore, in some examples, one or both of fins (298a, 298b) extend along only a portion or certain portions of channel (72). Other suitable configurations and positions for fins (298a, 298b) will be apparent to persons skilled in the art in view of the teachings herein.

In the example shown, fins (298a, 298b) are each formed as a separate element from cartridge deck (73) and are fixed to cartridge deck (73) by various suitable methods as will be apparent to persons skilled in the art in view of the teachings herein. For example, fins (298a, 298b) may be fixed to cartridge deck (73) via an adhesive. In some versions, fins (298a, 298b) may be overmolded onto the cartridge deck (73) or other parts of cartridge (270). In some versions, each fin (298a, 298b) is integral with cartridge (270). In some such versions, fins (298a, 298b) may be co-molded with cartridge deck (73) or other parts of cartridge (270). In the example shown, fins (298a, 298b) are configured to be rigid enough to maintain their position and urge tissue toward anvil (60) when an operator grasps tissue between anvil (60) and lower jaw (50). However, fins (298a, 298b) are also configured to be compressible a sufficient amount such that when an operator grasps tissue (90) between lower jaw (50) and anvil (60), fins (298a, 298b) do not prevent anvil (60) from moving to the fully closed position relative to the lower jaw (50) (as, for example, shown in FIGS. 12A-12C). Other suitable configurations of compressive feature (296) will be apparent to persons skilled in the art in view of the teachings herein.

In some examples, fins (298a, 298b) may comprise a polymer and/or an elastomer. In addition or in the alternative, fins (298a, 298b) may be formed of a resilient material, such that fins (298a, 298b) resiliently bias tissue (90) against anvil (60) when tissue (90) is captured between anvil (60) and deck (73). Other suitable materials that may be used to form fins (298a, 298b) will be apparent to persons skilled in the art in view of the teachings herein. It should be understood that, due to the compressibility and/or other properties of fins (298a, 298b), fins (298a, 298b) will not cause any trauma to tissue (90) even when fins (298a, 298b) compresses the tissue (90) against anvil (60). In the example shown, fins (298a, 298b) comprise the same material and same configuration (e.g., foam, etc.) as one another, but in some examples fin (298a) may be formed of a different material and/or configuration than fin (298b).

Figure 12A:
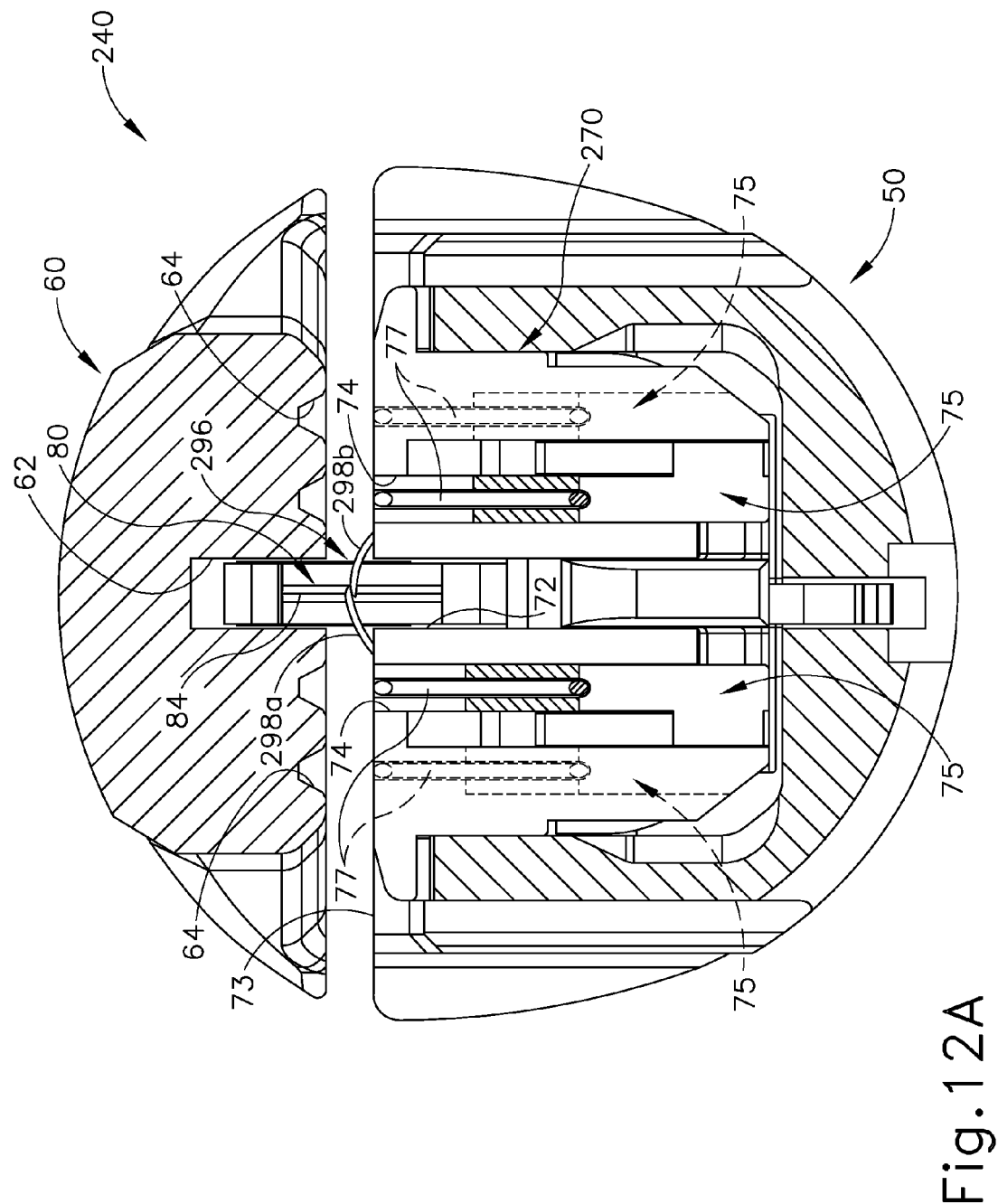
FIG. 12A depicts a cross-sectional end view of the end effector of FIG. 11, with a firing beam in a proximal position.
Figure 12B:
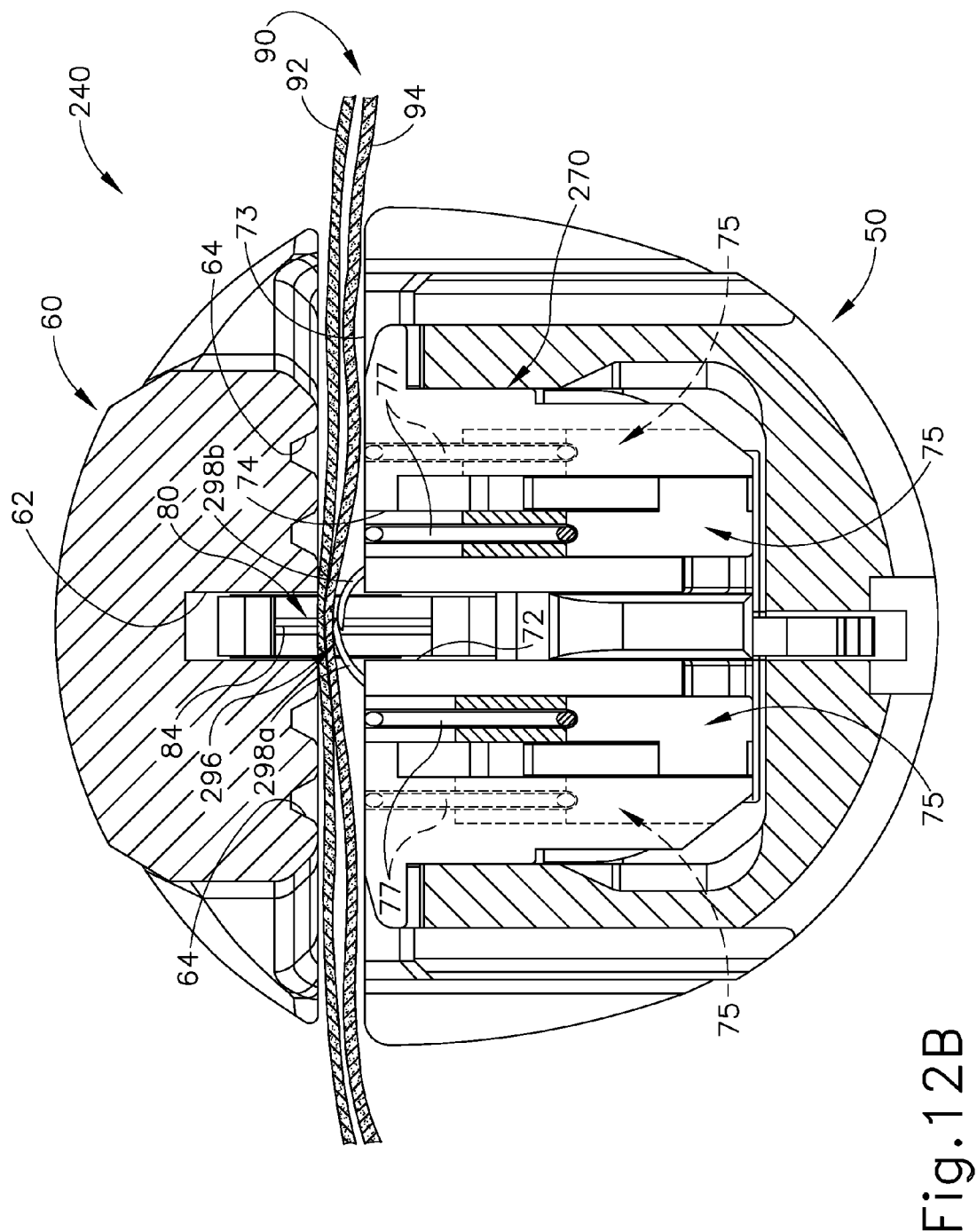
FIG. 12B depicts a cross-sectional end view of the end effector of FIG. 11, with the firing beam in a proximal position and tissue positioned between an anvil and a staple cartridge deck of the end effector.
Figure 12C:
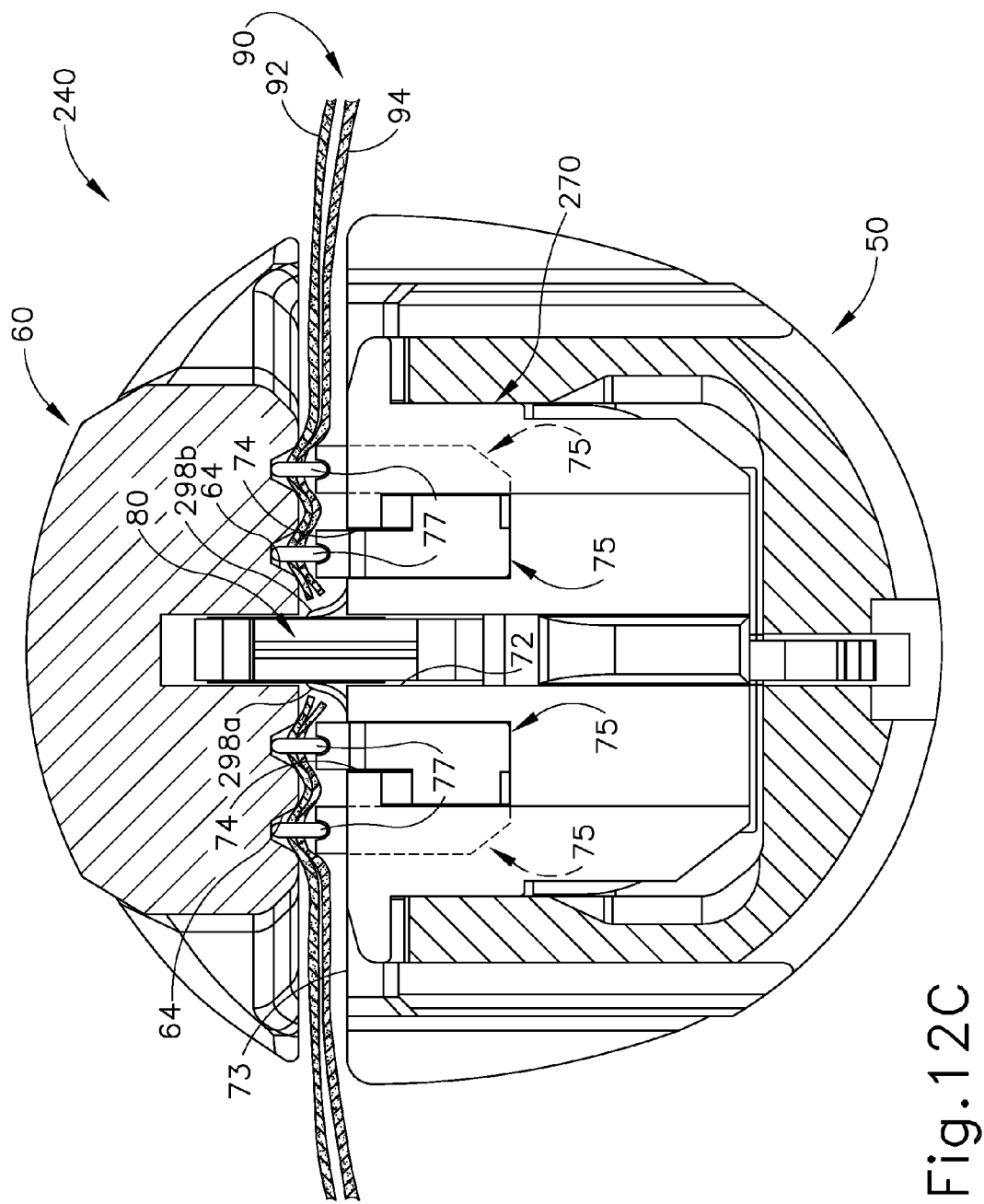
FIG. 12C depicts a cross-sectional end view of the end effector of FIG. 11, with the firing beam in a distal position and tissue positioned between the anvil and staple cartridge deck of the end effector.

Referring to FIGS. 12B-12C, in use, end effector (240) may be used to sever and staple tissue in the same manner as described above with respect to end effector (40). The layers (92, 94) of tissue (90) are initially positioned between anvil (60) and lower jaw (50). In the example shown, the combined thickness of the layers (92, 94) of tissue (90) along at least a portion of the tissue (90) is less than the predefined gap distance between anvil (60) and cartridge deck (73) when anvil (60) is in the closed position. However, as shown, fins (298a, 298b) apply a substantially vertical load to the portions of tissue (90) that are coincident with fins (298a, 298b), compressing the corresponding region of tissue (90) up against anvil (60).

In the example shown, compressible feature (296) contacts a region of tissue (90) that is substantially aligned with channels (62, 72). As shown in FIG. 12C, as knife member (80) advances along channels (62, 72), knife member (80) simultaneously severs tissue (90) and displaces fins (298a, 298b) away from the central, longitudinally extending vertical plane of end effector (240), such that fins (298a, 298b) are urged away from channel (72) and are positioned against respective sides of knife member (80). Moreover, knife member (80) drives wedge sled (78) distally as knife member (80) translates distally through end effector (240), thereby driving staples (77) through tissue and against anvil

(60) into formation, in the same manner described above with respect to end effector (40).

Compressible feature (296) prevents tissue (90) from substantially moving during the severing and stapling of tissue (90). In particular, by compressing tissue (90) against anvil (60), compressible feature (296) keeps the tissue (90) substantially stationary across the width of deck (73) and anvil (60), thereby preventing movement of tissue (90) along lateral paths that are transverse to the longitudinal axis of end effector (240). Moreover, compressible feature (296) prevents movement of tissue (90) along paths that are parallel to the longitudinal axis of end effector (240). By firmly holding the position of tissue (90) between anvil (60) and cartridge deck (73), compressible feature (296) may reduce stress that might otherwise be imposed on tissue (90), at the regions where legs of staples (77) are driven through tissue (90), as knife member (80) as driven through tissue. In other words, compressible feature (296), rather than staples (77), may serve the role of holding tissue (90) in place as knife member (80) cuts through the tissue (90). In the absence of compressible feature (296), when tissue (90) is thinner than the predefined gap separating the surface of cartridge deck (73) and the corresponding surface of anvil (60) when anvil (60) is in a closed position, staples (77) may need to serve the role of holding tissue (90) in place as knife member (80) cuts through the tissue (90), which may cause the tissue (90) to tear at staples (77) through a cheese wire effect. Such tearing may compromise the fixation of staples (77) in the tissue (90), which may ultimately result in full or partial failure of a deployed line of staples (77). Compressible feature (296) may thus maintain greater structural integrity of tissue (90) after end effector (240) has been actuated on the tissue (90); and may thus provide a more reliable line of staples (77) in the tissue.

In some versions, knife member (80) may include at least one feature that directs fins (298a, 298b) away from tissue (90) to prevent fins (298a, 298b) from substantially interfering with further advancement of knife member (80). Moreover, in some examples, knife member (80) and/or fins (298a, 298b) may include a lubricious coating to prevent fins (298a, 298b) from substantially interfering with further advancement of knife member (80). Other suitable configurations of fins (298a, 298b) will be apparent to persons skilled in the art in view of the teachings herein.

While compressible feature (296) is shown as being part of cartridge (270) in the present example, it should be understood that one or more similar compressible features may be readily incorporated into anvil (60). In versions where anvil (60) includes an integral compressible feature like compressible feature (296), cartridge (270) may still include compressible feature (296). In some such versions, the compressible feature(s) of anvil (60) may be laterally offset from compressible feature (296) of cartridge (270). In some other versions where anvil (60) includes one or more integral compressible features like compressible feature (296), cartridge (270) may simply lack compressible feature (296). Cartridge (270) may also include more than one compressible feature (196) at any suitable positions along the width of deck (73). It should also be understood that, regardless of whether the compressible feature(s) (296) is/are on anvil (60) and/or on cartridge (270), end effector (240) may be used as a tissue grasper by selectively opening and closing anvil (60), even with thin tissue structures, without necessarily firing knife member (80). Other suitable ways in which compressible feature (296) may be varied and used will be apparent to those of ordinary skill in the art in view of the teachings herein.

Figure 13:
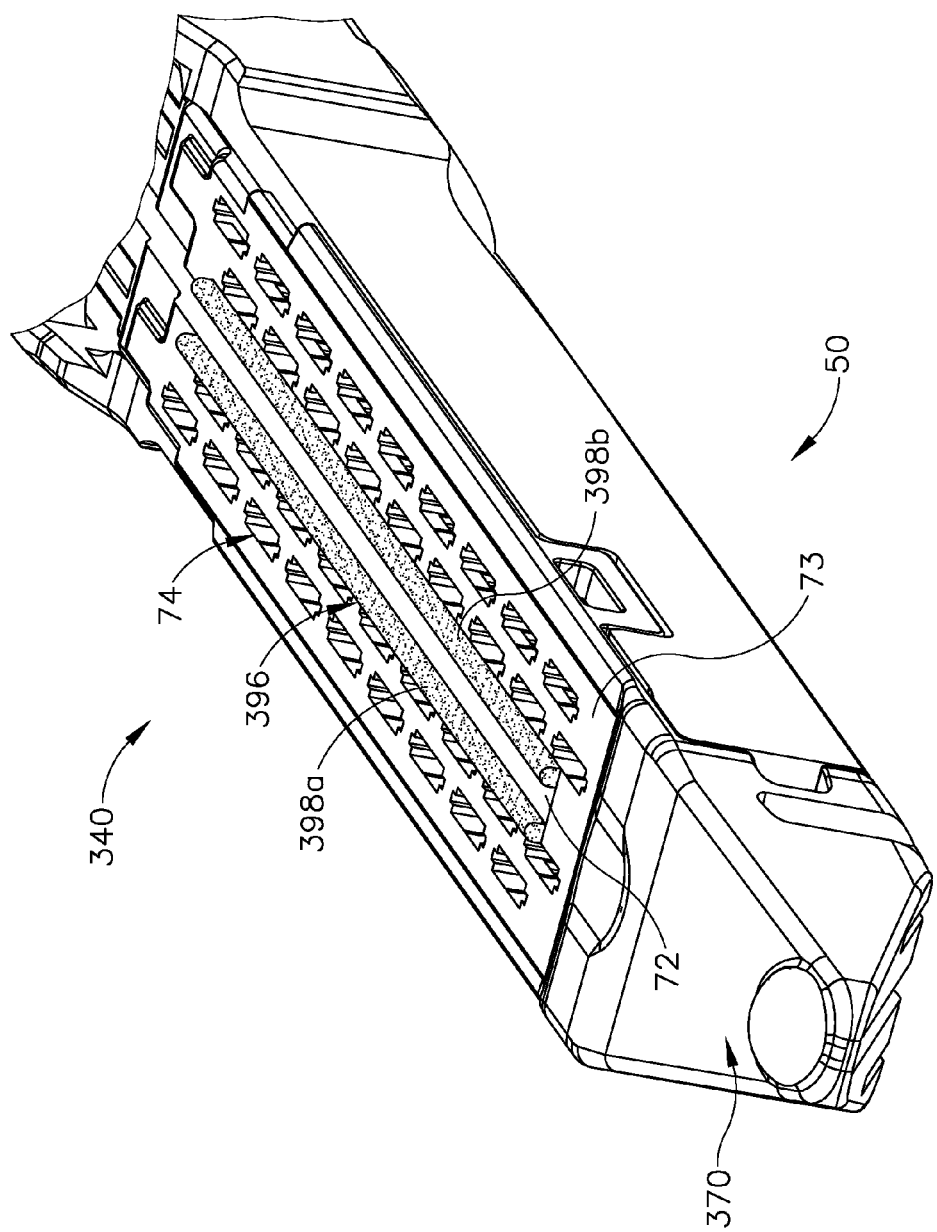
FIG. 13 depicts perspective view of another exemplary alternative end effector that may be incorporated into the instrument of FIG. 1, with an anvil of the end effector omitted for clarity.

C. Exemplary Staple Cartridge with Compressible Linear Elements Along Knife Slot FIGS. 13-14C show an exemplary alternative end effector (340). As discussed above, end effector (340) is configured to operate substantially similarly to end effector (40), except for the differences described below. End effector (340) comprises anvil (60) and lower jaw (50). Anvil (60) is omitted from FIG. 13 for clarity. An exemplary alternative staple cartridge (370) is disposed in lower jaw (50). Staple cartridge (370) is configured to operate in a substantially similar manner as discussed with respect to staple cartridge (70). However, staple cartridge (370) of this example includes a compressible feature (396) disposed along longitudinal channel (72) of cartridge (270).

Compressible feature (396) is configured to urge tissue captured between anvil (60) and lower jaw (50) toward anvil (60). Compressible feature (396) of the present example comprises a pair of compressible elongate members (398a, 398b). In the present example, elongate members (398a, 398b) are in the form of bumper rails. Elongate member (398a) is fixed to cartridge deck (73) on one side of channel (72) and extends longitudinally along the length of channel (72). Similarly, elongate member (398b) is fixed to cartridge deck (73) on another side of channel (72) and extends longitudinally along the length of channel (72). As shown, each elongate member (398a, 398b) extends upwardly from deck (73) and parallel to the longitudinal axis of end effector (340) and instrument (10). Each elongate member (398a, 398b) of the present example has a generally rectangular shape with rounded edges, in cross section (along a plane that is perpendicular to the longitudinal axis of end effector (340) and instrument (10)). Alternatively, any other suitable cross-sectional configuration may be used, including but not limited to triangular, semicircular, semi-elliptical, etc.

In the present example, each elongate member (398a, 398b) is formed as a single, elongate feature disposed substantially along the entire length of channel (72). However, in alternative examples, one or both of elongate members (398a, 398b) may be formed as a plurality of discrete elements that are spaced apart from each other along the length of channel (72). Furthermore, in some examples, one or both of elongate members (398a, 398b) extend along only a portion or certain portions of channel (72). Other suitable configurations of elongate members (398a, 398b) will be apparent to persons skilled in the art in view of the teachings herein.

In the example shown, elongate members (398a, 398b) are each formed as a separate element from cartridge deck (73) and are fixed to cartridge deck (73) by various suitable methods as will be apparent to persons skilled in the art in view of the teachings herein. For example, elongate members (398a, 398b) may be fixed to cartridge deck (73) via an adhesive. In some versions, elongate members (398a, 398b) may be overmolded onto the cartridge deck (73) or other parts of cartridge (370). In some versions, each elongate member (398a, 398b) is integral with cartridge (370). In some such examples, elongate members (398a, 398b) may be co-molded with cartridge deck (73) or other parts of cartridge (370). In the example shown, elongate members (398a, 398b) are configured to be rigid enough to maintain their positions and urge tissue toward anvil (60) when an operator grasps tissue between anvil (60) and lower jaw (50). However, elongate members (398a, 398b) are also configured to be compressible a sufficient amount such that when an operator grasps tissue (90) between lower jaw (50) and anvil (60), elongate members (398a, 398b) do not prevent anvil (60) from moving to the fully closed position relative to the lower jaw (50) (as, for example, shown in FIGS. 14A-14C).

In some examples, elongate members (398a, 398b) may comprise a polymer and/or an elastomer. In addition or in the alternative, elongate members (398a, 398b) may be formed of a resilient material, such that elongate members (398a, 398b) resiliently bias tissue (90) against anvil (60) when tissue (90) is captured between anvil (60) and deck (73). Other suitable materials that may be used to form elongate members (398a, 398b) will be apparent to persons skilled in the art in view of the teachings herein. It should be understood that, due to the compressibility and/or other properties of elongate members (398a, 398b), elongate members (398a, 398b) will not cause any trauma to tissue (90) even when elongate members (398a, 398b) compresses the tissue (90) against anvil (60). In the example shown, elongate members (398a, 398b) comprise the same material and same configuration (e.g., foam, etc.) as one another, but in some examples elongate member (398a) may be formed of a different material and/or configuration than elongate member (398b).

Figure 14A:
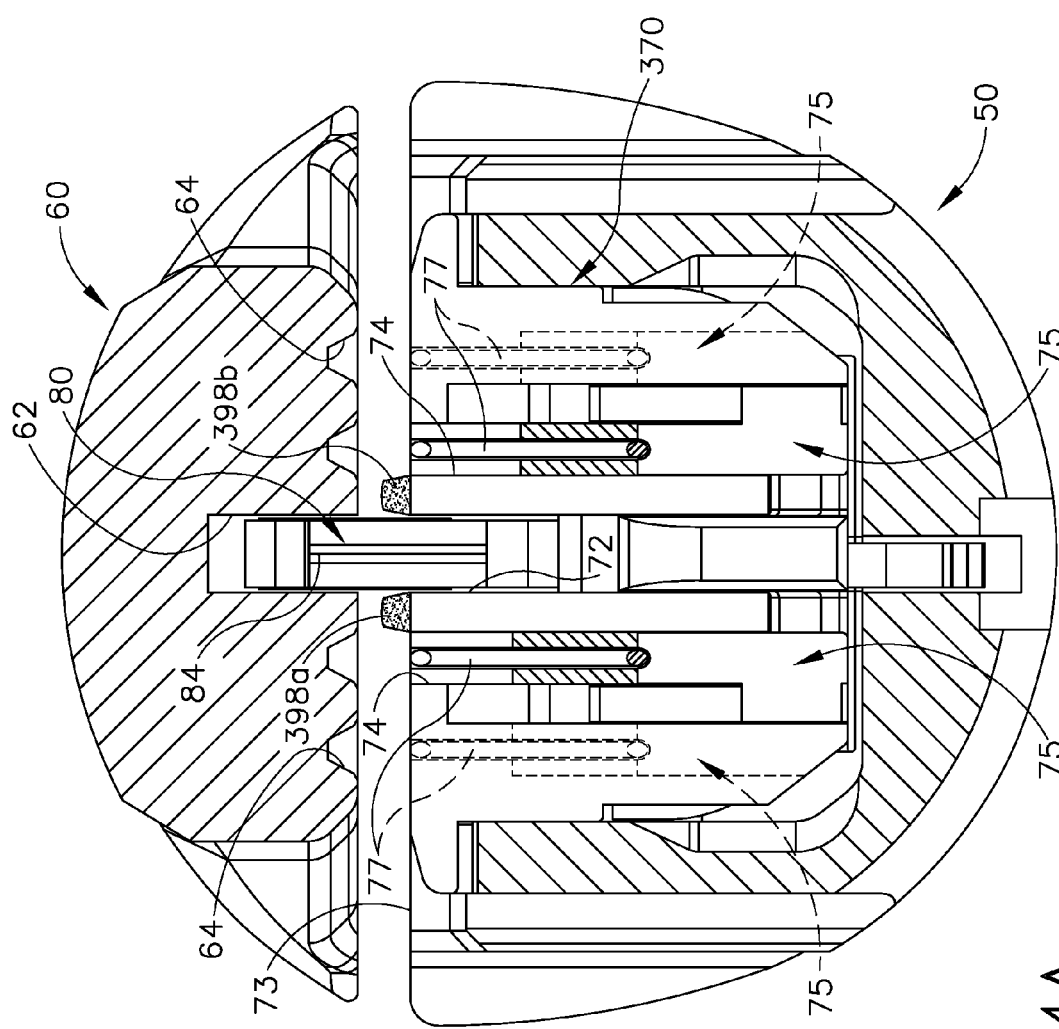
FIG. 14A depicts a cross-sectional end view of the end effector of FIG. 13, with a firing beam in a proximal position.
Figure 14B:
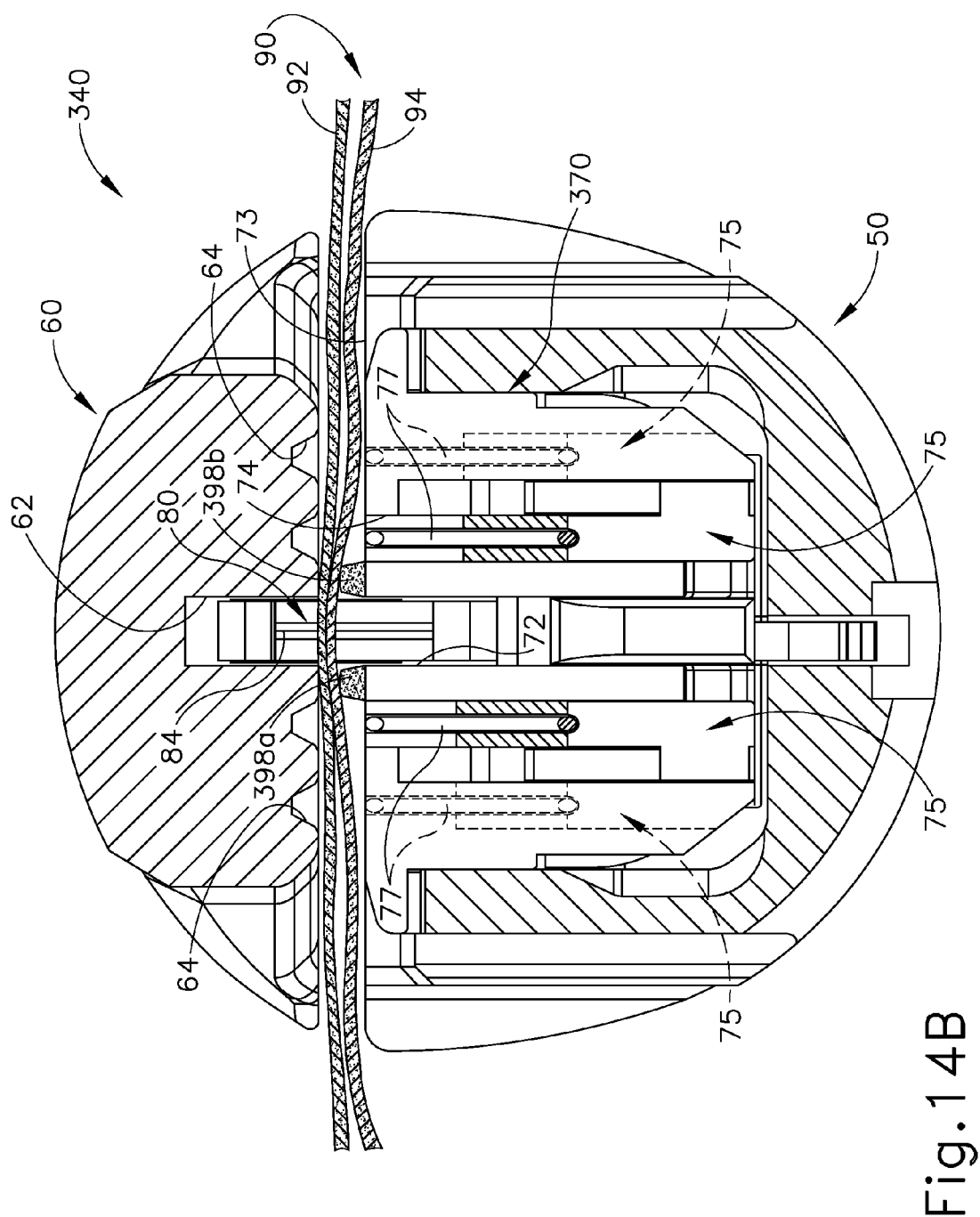
FIG. 14B depicts a cross-sectional view of the end effector of FIG. 13, with the firing beam in a proximal position and tissue positioned between an anvil and a staple cartridge deck of the end effector.
Figure 14C:
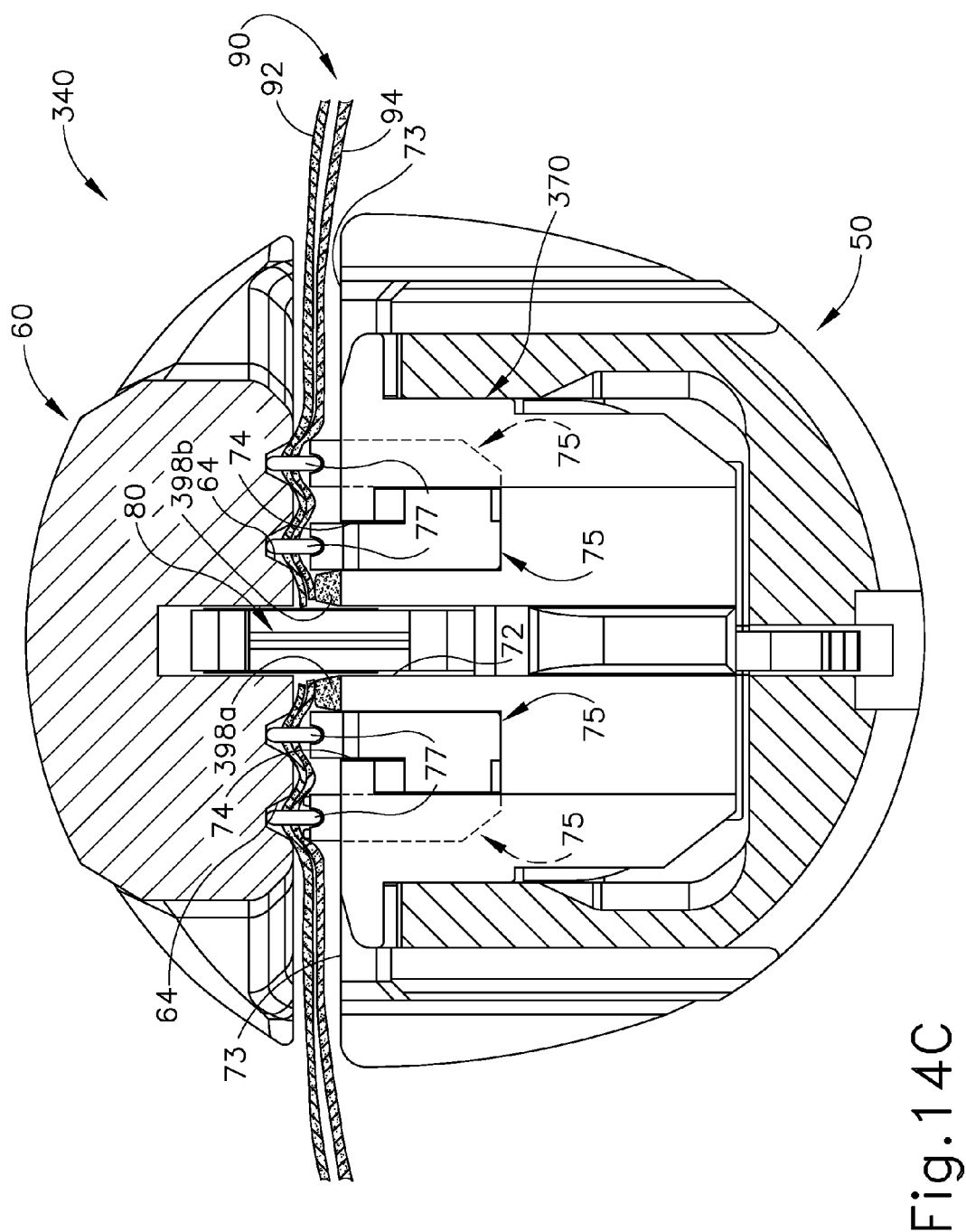
FIG. 14C depicts a cross-sectional view of the end effector of FIG. 13, with the firing beam in a distal position and tissue positioned between the anvil and staple cartridge deck of the end effector.

Referring to FIGS. 14B-14C, in use, end effector (340) may be used to sever and staple tissue in the same manner as described above with respect to end effector (40). The layers (92, 94) of tissue (90) are initially positioned between anvil (60) and lower jaw (50). In the example shown, the combined thickness of the layers (92, 94) of tissue (90) along at least a portion of the tissue (90) is less than the predefined gap distance between anvil (60) and cartridge deck (73) when anvil (60) is in the closed position. However, as shown, elongate members (398a, 398b) apply a substantially vertical load to the portions of tissue (90) that are coincident with elongate members (398a, 398b), compressing the corresponding region of tissue (90) up against anvil (60). Thus, as shown, elongate members (398a, 398b) urge portions of tissue that are positioned outwardly of channels (62, 72) against anvil (60). Elongate members (398a, 398b) thus provide two discrete areas of stability for tissue to remain in position as knife member (80) advances between elongate members (398a, 398b) and along channels (62, 72).

As shown in FIG. 14C, as knife member (80) advances along channels (62, 72), knife member (80) severs tissue (90). Moreover, knife member (80) drives wedge sled (78) distally as knife member (80) translates distally through end effector (340), thereby driving staples (77) through tissue and against anvil (60) into formation, in the same manner described above with respect to end effector (40). In some examples, knife member (80) and/or elongate members (398a, 398b) may include a lubricious coating as to not hamper advancement of the knife member (80).

Compressible feature (396) prevents tissue (90) from substantially moving during the severing and stapling of tissue (90). In particular, by compressing tissue (90) against anvil (60), compressible feature (396) keeps the tissue (90) substantially stationary across the width of deck (73) and anvil (60), thereby preventing movement of tissue (90) along lateral paths that are transverse to the longitudinal axis of end effector (340). Moreover, compressible feature (396) prevents movement of tissue (90) along paths that are parallel to the longitudinal axis of end effector (340). By firmly holding the position of tissue (90) between anvil (60) and cartridge deck (73), compressible feature (396) may reduce stress that might otherwise be imposed on tissue (90), at the regions where legs of staples (77) are driven through tissue (90), as knife member (80) as driven through tissue. In other words, compressible feature (396), rather than staples (77), may serve the role of holding tissue (90) in place as knife member (80) cuts through the tissue (90). In the absence of compressible feature (396), when tissue (90) is thinner than the predefined gap separating the surface of cartridge deck (73) and the corresponding surface of anvil (60) when anvil (60) is in a closed position, staples (77) may need to serve the role of holding tissue (90) in place as knife member (80) cuts through the tissue (90), which may cause the tissue (90) to tear at staples (77) through a cheese wire effect. Such tearing may compromise the fixation of staples (77) in the tissue (90), which may ultimately result in full or partial failure of a deployed line of staples (77). Compressible feature (296) may thus maintain greater structural integrity of tissue (90) after end effector (340) has been actuated on the tissue (90); and may thus provide a more reliable line of staples (77) in the tissue.

While compressible feature (396) is shown as being part of cartridge (370) in the present example, it should be understood that one or more similar compressible features may be readily incorporated into anvil (60). In versions where anvil (60) includes an integral compressible feature like compressible feature (396), cartridge (370) may still include compressible feature (396). In some such versions, the compressible feature(s) of anvil (60) may be laterally offset from compressible feature (396) of cartridge (370). In some other versions where anvil (60) includes one or more integral compressible features like compressible feature (296), cartridge (370) may simply lack compressible feature (396). It should also be understood that, regardless of whether the compressible feature(s) (396) is/are on anvil (60) and/or on cartridge (370), end effector (340) may be used as a tissue grasper by selectively opening and closing anvil (60), even with thin tissue structures, without necessarily firing knife member (80). Other suitable ways in which compressible feature (396) may be varied and used will be apparent to those of ordinary skill in the art in view of the teachings herein.

D. Exemplary Anvil with Displaceable, Compressible Fins Along Knife Slot

Figure 15:
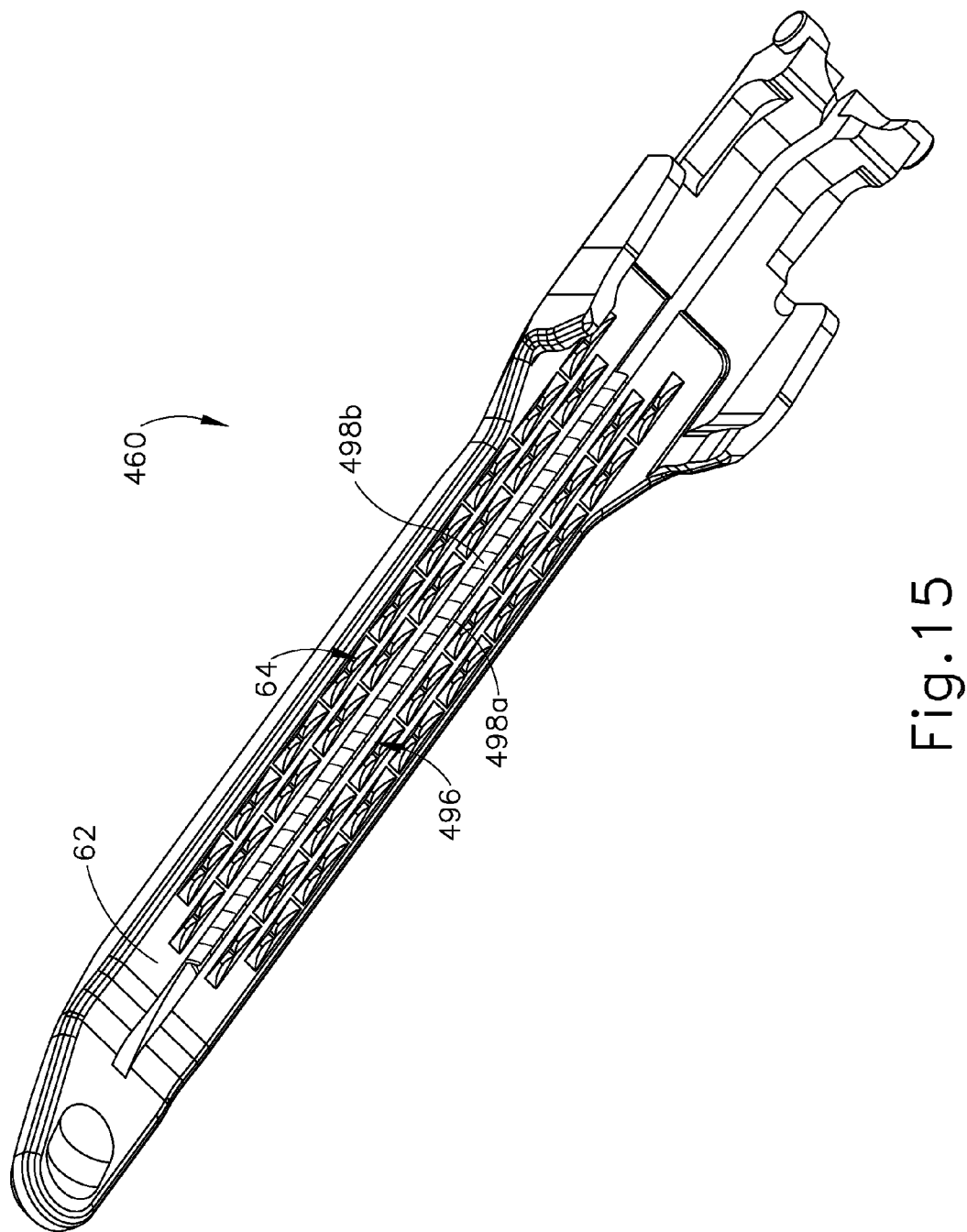
FIG. 15 depicts a perspective view of an exemplary alternative anvil that may be incorporated into the end effector of FIG. 3.
Figure 16A:
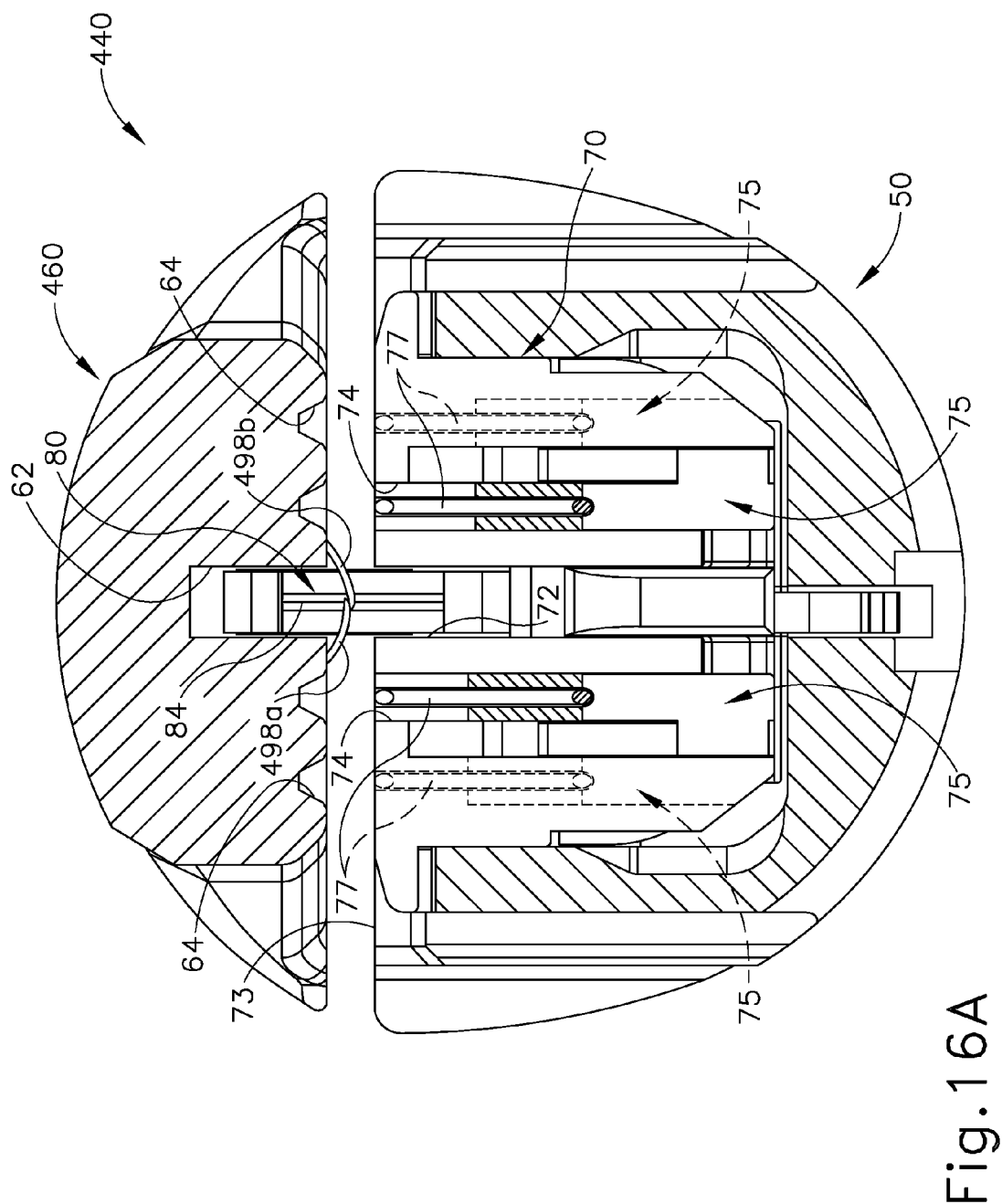
FIG. 16A depicts a cross-sectional end view of an exemplary alternative end effector incorporating the anvil of FIG. 16A, with a firing beam in a proximal position.
Figure 16B:
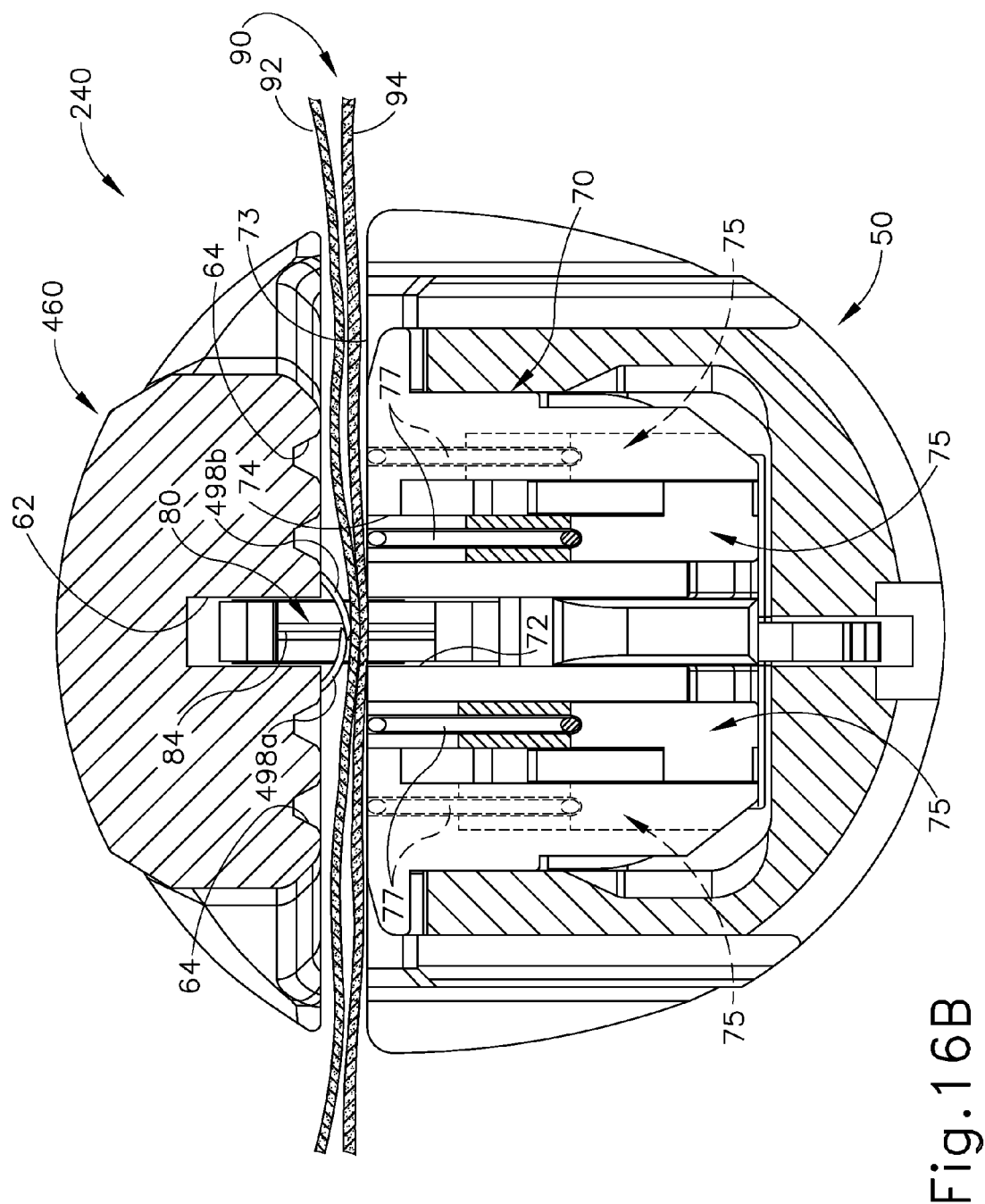
FIG. 16B depicts a cross-sectional view of the end effector of FIG. 16A, with the firing beam in a distal position and tissue positioned between an anvil and a staple cartridge deck of the end effector.
Figure 16C:
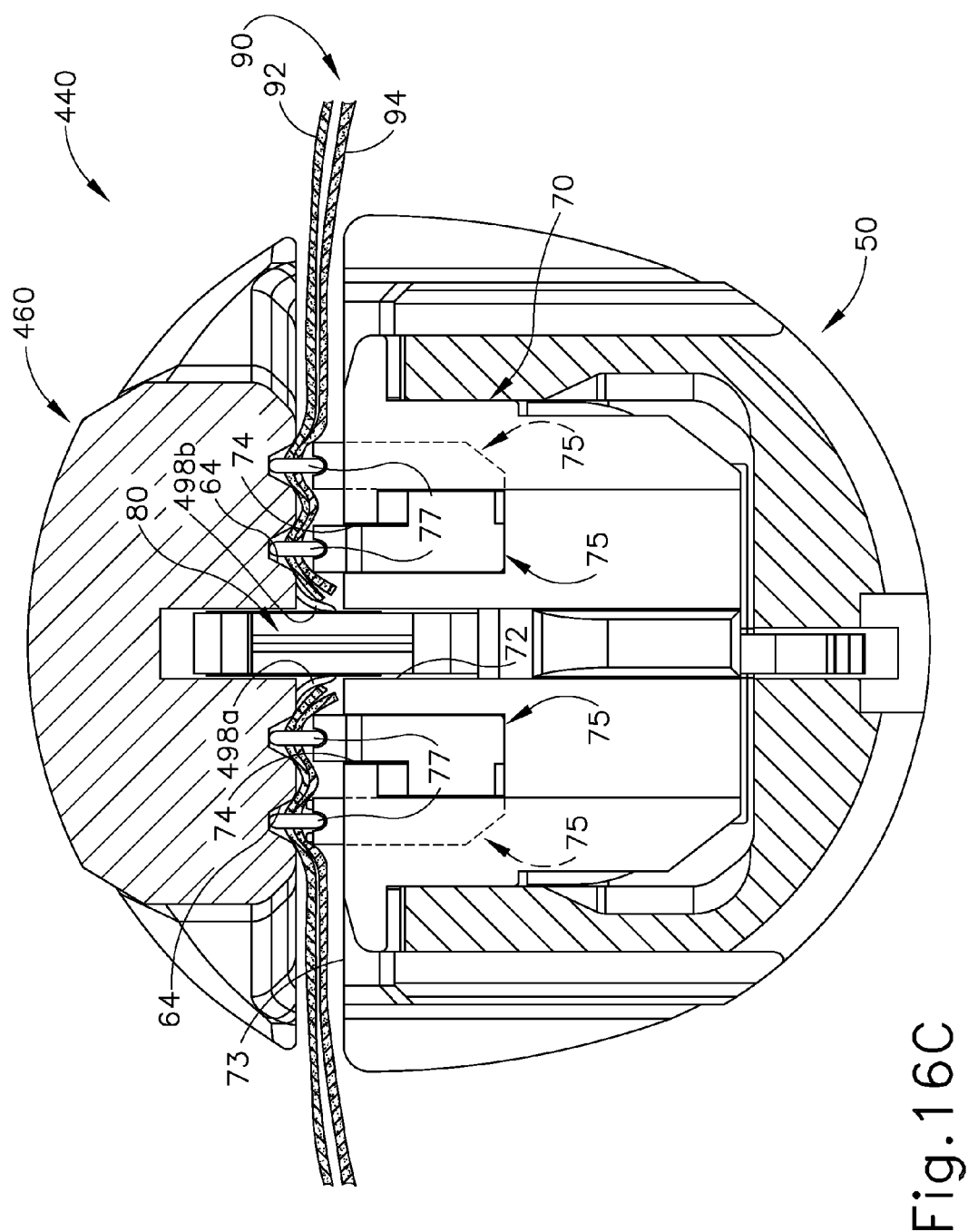
FIG. 16C depicts a cross-sectional view of the end effector of FIG. 16A, with the firing beam in a distal position and tissue positioned between the anvil and staple cartridge deck of the end effector.

FIG. 15 shows an exemplary alternative anvil (460) that may be incorporated into another exemplary alternative end effector (440), as shown in FIGS. 16A-16C. As discussed above, end effector (440) is configured to operate substantially similarly to end effector (40), except for the differences described below. End effector (440) comprises anvil (460) and lower jaw (50), which includes staple cartridge (70). Anvil (460) is configured to operate in a substantially similar manner as discussed with respect to anvil (60). However, anvil (460) of this example includes a compressible feature (496) disposed along longitudinal channel (62) of anvil (460).

Compressible feature (496) is configured to urge tissue that is captured between the anvil (60) and lower jaw (50) toward cartridge deck (73). Compressible feature (496) of the present example comprises a pair of opposing fins (498a, 498b). Fin (498a) is fixed to anvil (460) on one side of channel (62) and fin (498b) is fixed to anvil (460) on another side of channel (62). As shown, each of the fins (498a, 498b) inwardly toward a central, longitudinally extending vertical plane of end effector (440) and instrument (10). Fins (498a, 498b) thus together bridge channel (62). In addition, fins (498a, 498b) extend downwardly toward deck (73), such that compressible feature (496) is configured to urge tissue captured between the anvil (60) and lower jaw (50) toward deck (73).

In the present example, fins (498a, 498b) are in contact with one another. Prior to knife member (80) advancing along channel (62), fin (498b) overlies fin (498a) in a partially overlapping fashion. However, in other examples, fin (498a) may overlie fin (498b). In other examples, one of fins (498a, 498b) may not overlie the other. For example, fins (498a, 498b) may extend at least partially over channel (62) such that they are in contact but not overlapping one another, or such that they do not contact one another, for example.

Each fin (498a, 498b) is formed as a single, elongate feature disposed substantially along the entire length of channel (62). However, in alternative examples, one or both of fins (498a, 498b) may be formed as a plurality of discrete elements that are spaced apart from each other along the length of channel (62). Furthermore, in some examples, one or both of fins (498a, 498b) extend along only a portion or certain portions of channel (62). Other suitable configurations and positions for fins (498a, 498b) will be apparent to persons skilled in the art in view of the teachings herein.

In the example shown, fins (498a, 498b) are each formed as a separate element from anvil (460) and are fixed to anvil (460) by various suitable methods as will be apparent to persons skilled in the art in view of the teachings herein. For example, fins (498a, 498b) may be fixed to anvil (460) via an adhesive. In some versions, fins (498a, 498b) may be overmolded onto anvil (460). In some versions, each fin (498a, 498b) is integral with anvil (460). In some such versions, fins (498a, 498b) may be co-molded with anvil (460). In the example shown, fins (498a, 498b) are configured to be rigid enough to maintain their positions and urge tissue toward deck (73) when an operator grasps tissue between anvil (460) and lower jaw (50). However, fins (498a, 498b) are also configured to be compressible a sufficient amount such that when an operator grasps tissue (90) between lower jaw (50) and anvil (460), fins (498a, 498b) do not prevent anvil (460) from moving to the closed position relative to the lower jaw (50) (as, for example, shown in FIGS. 16A-16C).

In some examples, fins (498a, 498b) may comprise a polymer and/or an elastomer. In addition or in the alternative, fins (498a, 498b) may be formed of a resilient material, such that fins (498a, 498b) resiliently bias tissue (90) against deck (73) when tissue (90) is captured between anvil (60) and deck (73). Other suitable materials that may be used to form fins (498a, 498b) will be apparent to persons skilled in the art in view of the teachings herein. It should be understood that, due to the compressibility and/or other properties of fins (498a, 498b), fins (498a, 498b) will not cause any trauma to tissue (90) even when fins (498a, 498b) compresses the tissue (90) against deck (73). In the example shown, fins (498a, 498b) comprise the same material and same configuration (e.g., foam, etc.) as one another, but in some examples fin (498a) may be formed of a different material and/or configuration than fin (498b).

Referring to FIGS. 16B-16C, in use, end effector (440) may clamp tissue in the same manner as described above with respect to end effector (40). The layers (92, 94) of tissue (90) are initially positioned between anvil (460) and lower jaw (50). In the example shown, the combined thickness of the layers (92, 94) of tissue (90) along at least a portion of the tissue (90) is less than the predefined gap distance between anvil (460) and cartridge deck (73) when anvil (460) is in the closed position. However, as shown, fins (498a, 498b) apply a substantially vertical load to the portions of tissue (90) that are coincident with fins (498a, 498b), compressing the corresponding region of tissue (90) down against deck (73).

In the example shown, compressible feature (496) contacts a region of tissue (90) that is substantially aligned with channels (62, 72). As shown in FIG. 16C, as knife member (80) advances along channels (62, 72), knife member (80) simultaneously severs tissue (90) and displaces fins (498a, 498b) away from the central, longitudinally extending vertical plane of end effector (440), such that fins (498a, 498b) are urged away from channel (72) and are positioned against respective sides of knife member (80). Moreover, knife member (80) drives wedge sled (78) distally as knife member (80) translates distally through end effector (440), thereby driving staples (77) through tissue and against anvil (460) into formation, in the same manner described above with respect to end effector (40).

Compressible feature (496) prevents tissue (90) from substantially moving during the severing and stapling of tissue (90). In particular, by compressing tissue (90) against deck (73), compressible feature (496) keeps the tissue (90) substantially stationary across the width of deck (73) and anvil (460), thereby preventing movement of tissue (90) along lateral paths that are transverse to the longitudinal axis of end effector (440). Moreover, compressible feature (496) prevents movement of tissue (90) along paths that are parallel to the longitudinal axis of end effector (440). By firmly holding the position of tissue (90) between anvil (460) and cartridge deck (73), compressible feature (496) may reduce stress that might otherwise be imposed on tissue (90), at the regions where legs of staples (77) are driven through tissue (90), as knife member (80) as driven through tissue. In other words, compressible feature (496), rather than staples (77), may serve the role of holding tissue (90) in place as knife member (80) cuts through the tissue (90). In the absence of compressible feature (496), when tissue (90) is thinner than the predefined gap separating the surface of cartridge deck (73) and the corresponding surface of anvil (460) when anvil (460) is in a closed position, staples (77) may need to serve the role of holding tissue (90) in place as knife member (80) cuts through the tissue (90), which may cause the tissue (90) to tear at staples (77) through a cheese wire effect. Such tearing may compromise the fixation of staples (77) in the tissue (90), which may ultimately result in full or partial failure of a deployed line of staples (77). Compressible feature (496) may thus maintain greater structural integrity of tissue (90) after end effector (440) has been actuated on the tissue (90); and may thus provide a more reliable line of staples (77) in the tissue.

In some versions, knife member (80) may include at least one feature that directs fins (498a, 498b) away from tissue (90) to prevent fins (498a, 498b) from substantially interfering with further advancement of knife member (80). Moreover, in some examples, knife member (80) and/or fins (498a, 498b) may include a lubricious coating to prevent fins (498a, 498b) from substantially interfering with further advancement of knife member (80). Other suitable configurations of fins (498a, 498b) will be apparent to persons skilled in the art in view of the teachings herein III. Exemplary Combinations The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a body; (b) a shaft assembly extending distally from the body, wherein the shaft assembly defines a longitudinal axis; (c) an end effector, wherein the end effector comprises: (i) an anvil, and (ii) a lower jaw, wherein the anvil is pivotable toward the lower jaw to capture tissue between the anvil and the lower jaw; and (d) a staple cartridge coupled with the lower jaw, wherein the staple cartridge comprises: (i) a deck facing the anvil, and (ii) a plurality of staples positioned in a plurality of staple openings formed through the deck; wherein at least one of the anvil or the deck comprises a compressible feature extending toward the other of the anvil or the deck, wherein the at least one compressible feature of the anvil or the deck is configured to compress tissue against the other of the anvil or the deck.

EXAMPLE 2

The apparatus of Example 1, wherein the staple cartridge defines a channel, wherein the compressible feature extends at least partially along the channel in a direction that is parallel to the longitudinal axis.

EXAMPLE 3

The apparatus of Example 2, wherein the compressible feature comprises a single unitary member spanning laterally across the channel.

EXAMPLE 4

The apparatus of Example 2, wherein the compressible feature comprises a pair of elongate members extending along opposite sides of the channel.

EXAMPLE 5

The apparatus of Example 4, wherein the elongate members each comprise a fin.

EXAMPLE 6

The apparatus of any one or more of Examples 2 through 5, wherein the compressible feature spans laterally across the channel along an arc.

EXAMPLE 7

The apparatus of any one or more of Examples 2 through 6, further comprising a firing bar slidingly received in the channel and movable through the end effector to effect severing and stapling of the tissue.

EXAMPLE 8

The apparatus of Example 7, wherein the compressible feature is positioned relative to the channel such that the firing bar is configured to sever the compressible feature as the firing bar moves through the channel.

EXAMPLE 9

The apparatus of Example 7, wherein the compressible feature is positioned relative to the channel such that the firing bar is configured to displace the compressible feature away from a plane passing through the longitudinal axis.

EXAMPLE 10

The apparatus of any one or more of Examples 7 through 9, wherein the compressible feature is configured to remain on the anvil or the deck after the firing bar moves through the end effector to sever and staple tissue.

EXAMPLE 11

The apparatus of Example 2 or 10, wherein the compressible feature comprises a pair of bumper rails, wherein the bumper rails extend longitudinally along at least a portion of the length of the channel, wherein the bumper rails are positioned on opposite lateral sides of the channel.

EXAMPLE 12

The apparatus of Example 1, wherein the anvil defines a channel, wherein the compressible feature extends at least partially along the channel.

EXAMPLE 13

The apparatus of Example 1 or 12, wherein the deck presents a deck surface facing the anvil, wherein the compressible feature is integral with the deck surface.

EXAMPLE 14

The apparatus of any one or more of Examples 1 or 12 through 13, wherein the anvil presents an anvil surface facing the deck, wherein the compressible feature is integral with the anvil surface.

EXAMPLE 15

The apparatus of any one or more of Examples 1 through 14, wherein the compressible feature comprises a foam material.

EXAMPLE 16

The apparatus of any one or more of Examples 1 through 15, wherein the compressible feature comprises an elastomeric material.

EXAMPLE 17

The apparatus of any one or more of Examples 1 through 16, wherein the compressible feature is configured to deform in response to compression of tissue by the compressible feature.

EXAMPLE 18

An end effector for use with a surgical stapler, the end effector comprising: (a) a first jaw, wherein the first jaw comprises a first channel extending along a longitudinally extending plane; (b) a second jaw, wherein the second jaw comprises a second channel extending along the longitudinally extending plane, wherein the first channel and second channel are configured to slidingly receive a portion of a firing member, wherein the first jaw is pivotable toward the second jaw to capture tissue between the first and second jaws; and (c) a compressible feature positioned along one or both of the first and second channels, wherein the compressible feature is configured to urge tissue captured between the first and second jaws toward the other of the first or second jaws.

EXAMPLE 19

The end effector of Example 18, wherein the second jaw comprises a staple cartridge defining a cartridge deck, wherein the staple cartridge defines the second channel, wherein the compressible feature extends from the cartridge deck across the second channel.

EXAMPLE 20

A method of using a surgical instrument, wherein the surgical instrument comprises: (a) an end effector, wherein the end effector comprises: (i) an anvil defining an anvil channel, (ii) a lower jaw, wherein the anvil is configured to move toward and away from the lower jaw, and (iii) a staple cartridge disposed in the lower jaw, wherein the staple cartridge comprises: (A) a plurality of staples, and (B) a deck facing the anvil, wherein the staples are configured to pass through the deck, wherein the deck defines a deck channel, wherein the deck channel extends along a common plane with the anvil channel, and (iv) a compressible feature, wherein the compressible feature is positioned on the anvil or on the deck adjacent to the anvil channel or the deck channel; and (b) a firing member configured to translate along the anvil channel and the deck channel; the method comprising: (a) positioning tissue between the anvil and the lower jaw; (b) moving the anvil toward the jaw to place the anvil a closed position, wherein moving the anvil toward the jaw causes the compressible feature to compress the tissue against the anvil or the deck, wherein the compressible feature compresses in response to compressing the tissue; and (c) advancing the firing member through the anvil channel and the deck channel, wherein the firing member severs or displaces the compressible feature during advancement of the firing member.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013 the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using a surgical instrument, wherein the surgical instrument comprises:
    (a) an end effector, wherein the end effector comprises:
        (i) an anvil,
        (ii) a lower jaw, wherein the anvil and the lower jaw are configured to transition between an open position and a closed position for releasably capturing tissue therebetween,
        (iii) a staple cartridge disposed in the lower jaw, wherein the staple cartridge comprises:
            (A) a plurality of staples, and
            (B) a deck facing the anvil, wherein the staples are configured to pass through the deck, wherein the deck defines a deck channel, and
        (iv) a compressible feature, wherein the compressible feature is positioned on one of the deck or the anvil so as to not overlie the staples when the end effector is in the closed position,
the method comprising:
    (a) receiving tissue between the anvil and the lower jaw; and
    (b) closing the end effector to thereby clamp the tissue between the anvil and the deck, wherein closing the end effector causes the compressible feature to compress the tissue against one of the anvil or the deck, wherein the compressible feature compresses in response to compressing the tissue.

2. The method of claim 1, wherein compressing the tissue against one of the anvil or the deck with the compressible feature includes inhibiting movement of the compressed tissue relative to the anvil or the deck.

3. The method of claim 1, wherein the compressible feature is affixed to the one of the deck or the anvil, wherein the compressible feature projects toward the other of the anvil or the deck.

4. The method of claim 1, wherein the compressible feature extends longitudinally along at least a portion of the length of the deck channel.

5. The method of claim 1, wherein the compressible feature is secured to the deck along first and second opposed lateral sides of the deck channel.

6. The method of claim 1, wherein the compressible feature comprises a single unitary member that spans laterally across the deck channel.

7. The method of claim 1, wherein the compressible feature comprises a pair of elongate members that extend longitudinally along opposed lateral sides of the deck channel.

8. The method of claim 7, wherein the pair of elongate members comprises a pair of fins, wherein the fins confront one another above the deck channel.

9. The method of claim 1, wherein the surgical instrument further comprises a cutting member, wherein the method further comprises advancing the cutting member distally through the deck channel.

10. The method of claim 9, wherein the compressible feature remains secured to the one of the deck or the anvil following distal advancement of the cutting member through the deck channel and subsequent opening of the end effector.

11. The method of claim 9, wherein the compressible feature extends at least partially across the deck channel, wherein advancing the cutting member distally through the deck channel includes advancing the cutting member distally through the compressible feature to thereby sever or displace the compressible feature.

12. The method of claim 1, wherein the anvil includes an anvil channel extending longitudinally therealong, wherein the compressible feature extends longitudinally along the anvil channel.

13. The method of claim 12, wherein the compressible feature is secured to the anvil.

14. The method of claim 1, wherein the compressible feature comprises a resilient elastomeric material.

15. The method of claim 14, wherein the compressible feature comprises a foam material.

16. A method of using a surgical instrument, wherein the surgical instrument includes an end effector having an anvil, a lower jaw, and a staple cartridge received by the lower jaw and having an elongate channel and a plurality of staple openings, wherein one of the staple cartridge or the anvil includes a tissue engagement projection that extends along the elongate channel and toward the other of the staple cartridge or the anvil, wherein the end effector is actuatable between an open position and a closed position for releasably capturing tissue between the anvil and the staple cartridge, the method comprising:
   (a) receiving tissue between the anvil and the staple cartridge;
   (b) closing the end effector on the tissue such that the tissue engagement projection directly contacts and urges the tissue toward one of the anvil or the staple cartridge; and
   (c) while the end effector remains closed, driving staples from the staple cartridge into the tissue such that the staples do not capture the tissue engagement projection.

17. The method of claim 16, wherein the tissue engagement projection compresses in response to closure of the end effector on the tissue.

18. The method of claim 16, wherein the tissue engagement projection extends laterally over at least a portion of the elongate channel.

19. A method of using a surgical instrument, wherein the surgical instrument includes an end effector having an anvil, a lower jaw, a staple cartridge received by the lower jaw and having an elongate channel and a plurality of staple openings, a tissue engagement feature provided on one of the staple cartridge or the anvil, and a cutting member, wherein the end effector is actuatable between an open position and a closed position for releasably clamping tissue between the anvil and the staple cartridge, the method comprising:
   (a) receiving tissue between the anvil and the staple cartridge;
   (b) closing the end effector on the tissue such that the tissue engagement feature directly contacts and urges the tissue toward one of the anvil or the staple cartridge; and
   (c) advancing the cutting member distally through the elongate channel of the staple cartridge such that the cutting member passes through the tissue engagement feature while cutting the tissue, wherein the tissue engagement feature deflects laterally away from the cutting member in response to the distal advancement thereof.

20. The method of claim 19, wherein closing the end effector on the tissue includes compressing the tissue engagement feature.

* * * * *